US009566250B2

(12) United States Patent
Mahmood et al.

(10) Patent No.: US 9,566,250 B2
(45) Date of Patent: Feb. 14, 2017

(54) ARTIFICIAL TISSUE CONSTRUCTS COMPRISING ALVEOLAR CELLS AND METHODS FOR USING THE SAME

(71) Applicant: SANOFI PASTEUR VAXDESIGN CORPORATION, Orlando, FL (US)

(72) Inventors: Ayesha Mahmood, Orlando, FL (US); Anatoly Kachurin, Orlando, FL (US); William Warren, Orlando, FL (US); Russell Higbee, Orlando, FL (US)

(73) Assignee: SANOFI PASTEUR VAXDESIGN CORPORATION, Orlando, FL (US)

( * ) Notice: Subject to any disclaimer, the term of this patent is extended or adjusted under 35 U.S.C. 154(b) by 405 days.

(21) Appl. No.: 14/153,535

(22) Filed: Jan. 13, 2014

(65) Prior Publication Data
US 2014/0147482 A1 May 29, 2014

Related U.S. Application Data

(62) Division of application No. 12/173,921, filed on Jul. 16, 2008, now Pat. No. 8,647,837.

(60) Provisional application No. 60/949,944, filed on Jul. 16, 2007.

(51) Int. Cl.
*A61K 9/70* (2006.01)
*A61K 35/36* (2015.01)
*A61K 35/14* (2015.01)
*C12N 5/071* (2010.01)
*G01N 33/50* (2006.01)
*A61K 35/17* (2015.01)

(52) U.S. Cl.
CPC ............... *A61K 9/70* (2013.01); *A61K 35/17* (2013.01); *A61K 35/36* (2013.01); *C12N 5/0688* (2013.01); *G01N 33/5082* (2013.01); *C12N 2502/28* (2013.01); *C12N 2533/54* (2013.01); *G01N 2800/12* (2013.01)

(58) Field of Classification Search
None
See application file for complete search history.

(56) References Cited

U.S. PATENT DOCUMENTS

| | | |
|---|---|---|
| 5,008,116 A | 4/1991 | Cahn |
| 5,160,490 A | 11/1992 | Naughton et al. |
| 5,354,686 A | 10/1994 | Haberman |
| 5,562,910 A | 10/1996 | Daynes et al. |
| 5,725,856 A | 3/1998 | Hudziak et al. |
| 5,739,001 A | 4/1998 | Brown et al. |
| 5,750,329 A | 5/1998 | Quinn et al. |
| 6,177,282 B1 | 1/2001 | McIntyre |
| 6,274,378 B1 | 8/2001 | Steinman et al. |
| 6,479,064 B1 | 11/2002 | Atala |
| 6,541,225 B1 | 4/2003 | Li |
| 6,835,550 B1 | 12/2004 | Estell et al. |
| 2002/0155108 A1 | 10/2002 | Barbera-Guillem et al. |
| 2003/0109042 A1 | 6/2003 | Wu et al. |
| 2003/0147923 A1 | 8/2003 | Klaviniskis |
| 2003/0199006 A1 | 10/2003 | Britz et al. |
| 2003/0207287 A1 | 11/2003 | Short |
| 2004/0009943 A1 | 1/2004 | Semple et al. |
| 2004/0109876 A1 | 6/2004 | Yamamoto et al. |
| 2004/0234510 A1 | 11/2004 | Mochitate |
| 2005/0191743 A1 | 9/2005 | Wu et al. |
| 2005/0229264 A1 | 10/2005 | Chang et al. |
| 2005/0282148 A1 | 12/2005 | Warren et al. |
| 2006/0078540 A1 | 4/2006 | Warren et al. |
| 2006/0105454 A1 | 5/2006 | Son et al. ............... 435/325 |
| 2006/0270029 A1 | 11/2006 | Warren et al. |
| 2006/0275270 A1 | 12/2006 | Warren et al. |
| 2007/0015136 A1 | 1/2007 | Sanchez-Schmitz et al. |
| 2007/0141552 A1 | 6/2007 | Warren et al. |
| 2007/0154956 A1 | 7/2007 | Warren et al. |
| 2007/0178076 A1 | 8/2007 | Drake et al. |
| 2007/0218054 A1 | 9/2007 | Sukumar et al. |
| 2008/0008653 A1 | 1/2008 | Tew et al. |
| 2009/0011455 A1 | 1/2009 | Warren et al. |
| 2009/0104221 A1 | 4/2009 | El Shikh et al. |
| 2009/0117581 A1 | 5/2009 | Warren et al. |

FOREIGN PATENT DOCUMENTS

| | | |
|---|---|---|
| EP | 0358506 | 9/1989 |
| EP | 1013668 | 6/2000 |
| EP | 1437147 | 9/2002 |
| EP | 1970444 | 12/2006 |
| JP | 3-10674 | 1/1991 |

(Continued)

OTHER PUBLICATIONS

Ansel, et al., "A Chemokine-Driven Positive Feedback Loop Organizes Lymphoid Follicles", Nature, vol. 406, pp. 309-314 (2000).
Aydar et al. (2005) *J. Immunol.* 174, 5358-5366.
Badylak, S.F. et al., "*Small Intestinal Submucosa: A Substrate for in vitro Cell Growth*," J. Biomater. Sci. Polymer Edn. (1998), vol. 9, No. 8, pp. 863-878.
Bai et al., "*Generation of Dendritic Cells From Human Bone Marrow Mononuclear Cells: Advantages From Clinical Applications in Comparison to Peripheral Blood Monocyte Derived Cells*," International Journal of Oncology, (2002), 20(2), pp. 247-253.
Banchereau, et al., "Dendritic Cells and the Control of Immunity", Nature, vol. 392, pp. 245-252 (1998).
Banchereau, et al., "Immunobiology of Dendritic Cells", Annu. Rev. Immunol., vol. 18, pp. 767-811 (2000).

(Continued)

*Primary Examiner* — Robert A Zeman
(74) *Attorney, Agent, or Firm* — Wenderoth, Lind & Ponack, L.L.P.

(57) ABSTRACT

The present invention comprises artificial tissue constructs that serve as in vitro models of mammalian lung tissue. The artificial tissue constructs of the present invention comprise functionally equivalent in vitro tissue scaffolds that enable immunophysiological function of the lung. The constructs can serve as novel platforms for the study of lung diseases (e.g., interstitial lung diseases, fibrosis, influenza, RSV) as well as smoke- and smoking-related diseases. The artificial tissue constructs of the present invention comprise the two components of alveolar tissue, epithelial and endothelial cell layers.

20 Claims, 10 Drawing Sheets

(56) References Cited

FOREIGN PATENT DOCUMENTS

| | | |
|---|---|---|
| JP | 8-507860 | 8/1996 |
| WO | 94/20142 | 9/1994 |
| WO | 99/12972 | 3/1999 |
| WO | WO 99/15629 | 4/1999 |
| WO | WO 99/43788 | 9/1999 |
| WO | WO 99/49319 | 9/1999 |
| WO | WO 03/041568 | 5/2003 |
| WO | WO 03/050271 | 6/2003 |
| WO | WO 04/031361 | 4/2004 |
| WO | WO 04/101773 | 11/2004 |
| WO | 2005/013896 | 2/2005 |
| WO | 2005/072088 | 8/2005 |
| WO | WO 05/104755 | 11/2005 |
| WO | WO 07/075979 | 7/2007 |
| WO | 2007/108835 | 9/2007 |
| WO | WO 07/106559 | 9/2007 |
| WO | WO 07/146267 | 12/2007 |

OTHER PUBLICATIONS

Baumgarth, "A Two-Phase Model of B-Cell Activation", Immunological Review, vol. 176, pp. 171-180 (2000).

Benbrook et al., "Organotypic cultures represent tumor microenvironment for drug testing," Drug Discovery Today: Disease Models, 3(2), pp. 143-148 (2005).

Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).

Birkness et al., A Tissue Culture Bilayer Model to Study the Passage of Neisseria Meningitidis, Infection and Immunity, Feb. 1995, p. 402-409, vol. 63, No. 2.

Birkness et al., An In Vitro Tissue Culture Bilayer Model to Examine Early Events in Mycobacterium Tuberculosis Infection, Infection and Immunity, Feb. 1999, p. 653-658, vol. 67, No. 2.

Bogdan, et al., "Fibroblasts as Host Cells in Latent Leishmaniosis", J. Exp. Med., vol. 191, pp. 2121-2129 (2000).

Boni et al. (2006) Eur. J. Immunol. 36, 3157-3166.

Brandtzaeg, P. et al., "Mucosal B Cells: Phenotypic Characteristics, Transcriptional, Regulation, and Homing Properties," Immunological Reviews (2005), vol. 206, pp. 32-63.

Bromelow, K. V. et al., "Whole Blood Assay for Assessment of the Mixed Lymphocyte Reaction," Journal of Immunological Methods, (2001), 247(1-2), pp. 1-8.

Büchele, S. et al., "Presentation of Tetanus Toxoid to Autologous T Cells by Dendritic Cells Generated From Human Blood. Improved Specificity with Dendritic Cells Generated Without Fetal Calf Serum," Advances in Experimental Medicine and Biology, (1997), vol. 417, pp. 233-237.

Buchler et al. (2003) Vaccine, 21, 877-882.

Butcher, et al., "Lymphocyte Trafficking and Regional Immunity", Advances in Immunology, vol. 72, pp. 209-253 (1999).

Castro, et al., "Spleen-Derived Stromal Cells. Adhesion Molecules Expression and Lymphocyte Adhesion to Reticular Cells", Eur. J. Cell. Biol., vol. 74, 321-328 (1997).

Caux et al. (1995) J. Immunol. 155, 5427-5435.

Cayeux et al. (1999) Eur. J. Immunol. 29, 225-234.

Chen, et al., "A Film Tension Theory of Phagocytosis", Journal of Colloid and Interface Science, vol. 190, pp. 118-133 (1997).

Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).

Crivellato, et al., "Stromal Cell Organisation in the Mouse Lymph Node. A Light and Electron Microscopic Investigation Using the Zinc Iodide-Osmium Technique", J. Anat., vol. 190, pp. 85-92 (1997).

Cyster, "Chemokines and the Homing of Dendritic Cells to the T Cell Areas of Lymphoid Organs", J. Exp. Med. vol. 189, No. 3, pp. 447-450 (1999).

Cyster, et al., "Follicular Stromal Cells and Lymphocyte Homing to Follicles", Immunological Reviews, vol. 176, pp. 181-193 (2000).

Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).

Denkbas, et al., "Magnetic Chotosan Microspheres: Preparation and Characterization", Reactive & Functional Polymers, vol. 50, pp. 225-232 (2002).

Dubey et al. (2005) J. Clin. Endocrin & Met., 90, 247-255.

Dubois, et al., "Dendritic Cells Enhance Growth and Differentiation of CD40-Activated B Lymphocytes", J. Exp. Med., vol. 185, pp. 941-951 (1997).

Edelman et al, A Cultureal Renaissance: In Vitro Cell Biology Embraces Three-Dimensional Context. Exp Neurol. 2005, vol. 192, pp. 1-6.

El Shikh, M. et al., "Follicular Dendritic Cells Stimulated by Collagen Type I Develop Dendrites and Networks In Vitro," Cell and Tissue Research, (2007), 329(1), pp. 81-89.

Forster, et al., "CCR7 Coordinates the Primary Immune Response by Establishing Functional Microenvironments in Secondary Lymphoid Organs", Cell., vol. 99, pp. 23-33 (1999).

Fransson, et al., "Culture of Human Epidermal Langerhans Cells in a Skin Equivalent", British Journal of Dermatology, vol. 139, pp. 598-604 (1998).

Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion", Eur. J. Immunol., vol. 28, pp. 2331-2343 (1998).

Fulcher, et al., "B-Cell Activation Versus Tolerance—The Central Role of Immunoglobulin Receptor Engagement and T-Cell Help", Int. Rev. Immunol., vol. 15, pp. 33-52 (1997).

Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).

Furuyama, A. et al., "Assembly of Basement Membrane in vitro by Cooperation Between Alveolar Epithelial Cells and Pulmonary Fibroblasts," Cell Structure and Function (1997), vol. 22, pp. 603-614.

Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).

Garside, et al., "Visualization of Specific B and T Lumphocyte Interactions in the Lymph Node", Science, vol. 281, pp. 96-99 (1998).

Gergel, et al., "Activation of Endothelium by Borrelia burgdorferiIn Vitro Enhances Transmigration of Specific Subsets of T Lymphocytes", Infection and Immunity, vol. 69, pp. 2190-2197 (2001).

Gretz, et al., "Cords, Channels, Corridors and Conduits: Critical Architectural Elements Facilitating Cell Interactions in the Lymph Node Cortex", Immunological Reviews, vol. 156, pp. 11-24 (1997).

Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).

Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).

Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).

Gunn, et al., "Mice Lacking Expression of Secondary Lymphoid Organ Chemokine Have Defects in Lymphocyte Homing and Dendritic Cell Localization", J. Exp. Med., vol. 189, pp. 451-460 (1999).

(56) References Cited

OTHER PUBLICATIONS

Gunzer, et al., "Antigen Presentation in Extracellular Matrix: Interactions of T Cells with Dendritic Cells are Dynamic, Short Lived, and Sequential", Immunity, vol. 13, pp. 323-332 (2000).
Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).
Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).
Jenkins, et al., "In Vivo Activation of Antigen-Specific CD4 T Cells", Annu. Rev. Immunol., vol. 19, pp. 23-45 (2001).
Junt, et al., "Antiviral Immune Responses in the Absence of Organized Lymphoid T Cell Zones in plt/pltMice", The Journal of Immunology, vol. 168, pp. 6032-6040 (2002).
Kabashima, et al., "Prostaglandin $E_2$-EP4 Signaling Initiates Skin Immune Responses by Promoting Migration and Maturation of Langerhans Cells", Nature Medicine, vol. 9, pp. 744-749 (2003).
Kadowaki, et al., "Subsets of Human Dendritic Cell Precursors Express Different Toll-Like Receptors and Respond to Different Microbial Antigens", J. Exp. Med. vol. 194, No. 6, pp. 863-869 (2001).
Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).
Kim et al., "*Three-Dimensional Tissue Culture Models in Cancer Biology*," Seminars in Cancer Biology, (2005), 15(5), pp. 365-377.
Kim, H.-J. et al, Establishment of Early Lymphoid Organ Infrastructure in Transplanted Tumors Mediated by Local Production of Lymphotoxin α and in Combined Absence of Functional B and T Cells. In J. of Immunology, vol. 172:4037-4047 (2004).
Kosco, M. H. et al., "*Folicular Dendritic Cell-Dependent B-Cell Proliferation and In Vitro Germinal Center*," Lymphatic Tissues In Vivo Immune Responses, (1991), pp. 687-690.
Kosco, M. H. et al., "*Follicular Dendritic Cell-Dependent Adhesion and Proliferation of B Cells In Vitro*," Journal of Immunology, (1992), 148(8), pp. 2331-2339.
Kosco, M. H. et al., "*Follicular Dendritic Cells and Germinal Center Formation In-Vitro*," Accessory Cells in HIV and Other Retroviral Infections: Morphological and Functional Aspects; Workshop on Morphological and Functional Aspects of Accessory Cells in retroviral Infections, Hamberg, Germany, 23-24, p. 44-49 (1991).
Kosco-Vilbois, "Are Follicular Dendritic Cells Really Good for Nothing", Nature Reviews Immunology, vol. 3, pp. 764-769 (2003).
Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).
Larsson, et al., "Requirement of Mature Dendritic Cells for Efficient Activation of Influenza A-Specific Memory CD8 + T Cells", The Journal of Immunology, vol. 165, pp. 1182-1190 (2000).
LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).
Levenberg, S. et al., "*Advances in Tissue Engineering*," Current Topics in Developmental Biology, (2004), vol. 61, pp. 113-134.
Luk, et al., "Rapid and Sensitive Detection of *Salmonella*(O:6,7) by Immunomagnetic Monoclonal Antibody-Based Assays", Journal of Immunological Methods, vol. 137, pp. 1-8 (1991).
Lukas, et al., "Human Cutaneous Dendritic Cells Migrate Through Dermal Lymphatic Vessels in a Skin Organ Culture Model", The Journal of Investigative Dermatology, vol. 106, pp. 1293-1299 (1996).
Manna, P. et al., "Differentiation and Functional Maturation of Human CD14<+> Adherent Peripheral Blood Monocytes by Xenogeneic Endothelial Cells: Up-Regulation of Costimulation Cytokine Generation, and Toll-Like Receptors," Transplantation, (2002), 74(2), pp. 243-252.
Matsumoto, et al., "Affinity Maturation Without Germinal Centres in Lymphotoxin-α-Deficient Mice", Nature, vol. 382, pp. 462-466 (1996).
Mebius, "Organogenesis of Lymphoid Tissues", Nat. Rev. Immunol, vol. 3, pp. 292-303 (2003).
Mellman, et al., "Dendritic Cells: Specialized and Regulated Antigen Processing Machines", Cell, vol. 106, pp. 255-258 (2001).
Miller, et al., "Two-Photon Imaging of Lymphocyte Motility and Antigen Response in Intact Lymph Node", Science, vol. 296, pp. 1869-1873 (2002).
Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).
Moser et al. (2000) *Nature Immunol.* 1, 199-205.
Nakamura, M. et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.
Nakatsu, M. N. et al., "*Angiogenic Sprouting and Capillary Lumen Formation Modeled by Human Umbilical Vein Endothelial Cells (HUVEC) in Fibrin Gels: The Role of Fibroblasts and Angiopoietin-1*," Microvascular Research (2003), vol. 66, pp. 102-112.
Neves, A. R. et al., "*Dendritic Cells Derived From Metastatic Cancer Vaccinated with Allogeneic Dendritic Cell-Autologous Tumor Cell Hybrids Express More CD86 and Induce Higher Levels of Interferon-Gamma in Mixed Lymphocyte Reactions*," Cancer Immunology and Immunotherapy, (2005), 54(1), pp. 61-66.
Oehler et al. (2000) *Ann. Hematol.*, 79, 355-362.
Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.
Parker, "T Cell-Dependent B Cell Activation", Annu. Rev. Immunol., vol. 11, pp. 331-360 (1993).
Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).
Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).
Podgrabinska, et al., "Molecular Characterization of Lymphatic Endothelial Cells", Proc. Natl. Acad. Sci. U.S.A., vol. 99, No. 25, pp. 16069-16074 (2002).
Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.
Poznansky, et al., "Efficient Generation of Human T Cells From a Tissue-Engineered Thymic Organoid", Nature Biotechnology, vol. 18, pp. 729-734 (2000).
Qu, et al., "Autocrine Type I IFN and Contact with Endothelium Promote the Presentation of Influenza A Virus by Monocyte-Derived APC", The Journal of Immunology, vol. 170, pp. 1010-1018 (2003).
Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).
Randolph, et al., "A Soluble Gradient of Endogenous Monocyte Chemoattractant Protein-1 Promotes the Transendothelial Migration of Monocytes In Vitro", The Journal of Immunology, vol. 155, pp. 3610-3618 (1995).
Randolph, et al., "Differentiation of Monocytes into Dendritic Cells in a Model of Transendothelial Trafficking", Science, vol. 282, pp. 480-483 (1998).

(56) References Cited

OTHER PUBLICATIONS

Randolph, et al., "Mononuclear Phagocytes Egress from an In Vitro Model of the Vascular Wall by Migrating Across Endothelium in the Basal to Apical Direction: Role of Intercellular Adhesion Molecule 1 and the CD11/CD18 Integrins", J. Exp. Med., vol. 183, pp. 451-462 (1996).
Randolph, et al., "Role of Tissue Factor in Adhesion of Mononuclear Phagocytes to and Trafficking Through Endothelium in Vitro", Blood, vol. 92, pp. 4167-4177 (1998).
Randolph, et al., "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).
Razanajaona, et al., In Vitro Triggering of Somatic Mutation in Human Naïve B Cells', The Journal of Immunology, vol. 159, pp. 3347-3353 (1997).
Regnier, et al., "Integration of Langerhans Cells into a Pigmented Reconstructed Human Epidermis", The Journal of Investigative Dermatology, vol. 109, No. 4, pp. 510-512 (1997).
Robbiani, et al., "The Leukotriene C4 Transporter MRP1 Regulates CCL19 (MIP-3β, ELC)-Dependent Mobilization of Dendritic Cells to Lymph Nodes", Cell, vol. 103, pp. 757-768 (2000).
Roos et al. (2005) *Expert Opin. Drug Metab. Toxicol.* 1, 187-202.
Rot, "In Situ Binding Assay for Studying Chemokine Interactions with Endothelial Cells", Journal of Immunological Methods, vol. 273, pp. 63-71 (2003).
Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).
Safarik, et al., "Use of Magnetic Techniques for the Isolation of Cells", Journal of Chromatography B, vol. 722, pp. 33-53 (1999).
Santini et al. (2000) *J. Exp. Med.* 191, 1777-1788.
Sarradell et al. (2003) *Vet. Pathol.*, 40, 395-404.
Seguin, R. et al., "*Human Brain Endothelial Cells Supply Support for Monocyte Immunoregulartory Functions*," Journal of Neuroimmunology, (2003), 135(1-2), pp. 96-106.
Sieben, et al., "Comparison of Different Particles and Methods for Magnetic Isolation of Circulating Tumor Cells", Journal of Magnetism and Magnetic Materials, vol. 225, pp. 175-179 (2001).
Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).
Skibinski, et al., "The Role of Hepatocyte Growth Factor and Its Receptor c-met in Interactions Between Lymphocytes and Stromal Cells in Secondary Human Lymphoid Organs", Immunology, vol. 102, pp. 506-514 (2001).
Soderberg, O. et al., "*The Human Follicular Dendritic Cell Line FDC-1 Binds Immune Complexes and Promotes Somatic Hypermutation,*" Blood, (2001), 98(11 part 2), pp. 40b.
Sprent, et al., "Antigen-Induced Selective Recruitment of Circulating Lymphocytes", Cellular Immunology, vol. 2, pp. 171-181 (1971).
Stoll, et al., "Dynamic Imaging of T Cell-Dendritic Cell Interactions in Lymph Nodes", Science, vol. 296, pp. 1873-1876 (2002).
Stuart, et al., "The Human Reticular Cell: Morphology and Cytochemistry", J. Pathol, vol. 103, pp. 41-47 (1971).
Suematsu, et al., "Generation of a Synthetic Lymphoid Tissue-Like Organoid in Mice", Nature Biotechnology, vol. 22, No. 12, pp. 1539-1545 (Dec. 2004).
Tan et al. (2005) *J. Leuk. Biol.* 78, 319-324.
Tarte et al., Leukemia, vol. 14, 2000, abstract p. 2182.
Tew et al. (2001) *Trends Immunol.* 22, 361-367.
Tew, J. G. et al., "*Follicular Dendritic Cells as Accessory Cells,*" Immunological Reviews, (1990), No. 117, pp. 185-211.
Tew, J.G. et al., "*Follicular Dendritic Cells and Presentation of Antigen and Costimulatory Signals to B Cells,*" Immunological Reviews (1997), vol. 156, pp. 39-52.

Thompson, H.G. et al., "*A Three-dimensional in vitro Model of Angiogenesis in the Airway Mucosa,*" Pulmonary Pharmacology & Therapeutics (2007), vol. 20, pp. 141-148.
Toyama, et al., "Memory B Cells Without Somatic Hypermutation are Generated from Bcl 6 Deficient B Cells", Immunity, vol. 17, pp. 329-339 (2002).
Tsunoda, R. et al., "*Follicular Dendritic Cells In Vitro Modulate the Expression of Fas and Bcl-2 on Germinal Center B Cells,*" Cell and Tissue Research, (2000), 299(3), pp. 395-402.
Tsunoda, R. et al., "*Human Follicular Dendritic Cells In Vitro and Follicular Dendritic-Cell-Like Cells,*" Cell and Tissue Research, (1997), 288(2), pp. 381-389.
Van Den Berg, et al., "Localization of β 1 Integrins and Their Extracellular Ligands in Human Lymphoid Tissues", American Journal of Pathology, vol. 143, pp. 1098-1110 (1993).
Weppler et al., Modulation of Endotoxin-Induced Neutrophil Transendothelial Migration by Alveolar Epithelium in a Defined Bilayer Model, *Experimental Lung Research* 32:10, 455-482 (2006).
West, et al., " Polymeric Biomaterials with Degradation Sites for Proteases Involved in Cell Migration", Macromolecules, vol. 32, pp. 241-244 (1999).
Wu et al. (2008) *J. Immunol.* 180, 281-290.
Wu, Y. et al., "*Influence of Follicular Dendritic Cells and Primed T Cells on Somatic Hypermutation In In Vitro Germinal Centers,*" Journal of Immunology, (2006), 176(suppl. S), pp. S235-S236.
Zhang, S. et al., "*Growth Factors Secreted by Bronchial Epithelial Cells Control Myofibroblast Proliferation: An in vitro Co-culture Model of Airway Remodeling in Asthma,*" Laboratory Investigation (1999), vol. 79, No. 4, pp. 395-405.
Weppler et al., Modulation of Endotoxin-Induced Neutrophil Transendothelial Migration by Alveolar Epithelium in a Defined Bilayer Model, Experimental Lung Research 32:10, 455-482 (2006).
Dubois et al., J. Leukocyte Biology, 1999, v.66, p. 224-230.
Gansuvd et al., Human Immunol., 2003, v.64, p. 427-439.
Clayton et al., Clin. Exp. Immunol., 2003, v.132, p. 174-179.
D'Amico et al., Blood 92:207-214 (1998).
Simmingskoeld et al., Scand. J. Immunol. 7:233-238 (1978).
Transwell® Permeable Supports Selection and Use Guide, Corning Corp., pp. 1-12 (2009).
Khademhosseini et al., "Microscale Technologies for Tissue Engineering and Biology," Proc. Natl. Acad. Sci. USA, vol. 103, pp. 2480-2487 (2006).
Takeuchi et al., CCL21 Chemokine Regulates Chemokine Receptor CCR7 Bearing Malignant Melanoma Cells, Clin. Cancer Res. 10:2351-2358 (2004).
Katakai et al., Lymph Node Fibroblastic Reticular Cells Construct the Stromal Reticulum via Contact with Lymphocytes, J. Exp. Med. 200(6):783-795 (2004).
Caux et al., Functional CD40 on B Lymphocytes and Dendritic Cells, Res. Immunol. 145:235-239 (1994).
Inaba et al., Clustering of Dendritic Cells, Helper T Lymphocytes, and Histocompatible B Cells During Primary Antibody Response In vitro, J. Exp. Med. 160:858-876 (1984).
Grouard et al., Regulation of Human B Cell Activation by Follicular Dendritic Cell and T Cell Signals, Curr. Topic Microbiol. Immunol. 201:105-117 (1995).
Warren, W., The Front-End of Vaccine Manufacturing: Getting Good Candidates from the Get-Go. Workshop on Science and Technology in North American Rapid Vaccine Manufacturing, Jan. 26, 2007.
Hashimoto, K., et al., Direct Observation and Analysis of Spatiotemporal Dynamics of Individual Living Monocyte During Transendothelial Migration. Atherosclerosis 177(1):19-27 (Nov. 2004).
Hashimoto, K., et al., Direct Observation and Analysis of Spatiotemporal Dynamics of Individual Living Monocyte During Transendothelial Migration. Collection of Papers from 16th Bioengineering Conference, Jan. 21, 2004, pp. 13-14.
Higbee, R., et al., An Immunologic Model for Rapid Vaccine Assessment—A Clinical Trial in a Test Tube. ALTA 37, Suppl. 1,19-27 (2009).

(56) References Cited

OTHER PUBLICATIONS

Schwiebert, L.M. et al. Modulation of MHC class II expression in human cells by dexamethasone. Cell Immunol. 165:12-19 (1995).

Kim, J. et al. Constitutive and inducible expression of B7 family of ligands by human airway epithelial cells. Am J Respir Cell Mol Biol. 33:280-289 (2005).

Salik, E. et al. Antigen trafficking and accessory cell function in respiratory epithelial cells. Am J Respir Cell Mol Biol. 21:365-379 (1999).

Cunningham, A.C. et al. A comparison of the antigen-presenting capabilities of class II MHC-expressing human lung epithelial and endothelial cells. Immunology 91:458-463 (1997).

Dugger, K. et al. Epithelial cells as immune effector cells: The role of CD40. Semin Immunol. 21(5): 289-292 (2009).

Price, N. et al., Genome-scale microbial in silico models: the constraints-based approach, TRENDS Biotechnol., 2003, vol. 21, No. 4, pp. 162-169.

Nagashima, U. et al., The cutting edge of molecular simulation What can molecular simulation tell us? From micro to macro—From the nature of the molecule to the nature of assembly, Chemical Engineering, 2003, vol. 67, No. 8, pp. 432-435.

Tomita, M. et al., Computer Simulation of Cells, CICSJ Bull., 2001, vol. 19, No. 6, pp. 2-6.

Sun, W.D. et al., An artificial immune system architecture and its applications, IECE Trans. Fundamentals, 2003, vol. E86-A, No. 7, pp. 1858-1868.

Guidry, A.J. et al., A bovine mammary endothelial/epithelial cell culture model of the blood/milk barrier, Can. J. Vet. Res., 1998, vol. 62, pp. 117-121.

Hauser, A. et al., Chemotactic responsiveness toward ligands for CXCR3 and CXCR4 is regulated on plasma blasts during the time course of a memory immune response, J. Immunol., 2002, vol. 169, pp. 1277-1282.

Alt, C. et al., Functional expression of the lymphoid chemokines CCL19 (ELC) and CCL21 (SLC) at the blood-brain barrier suggests their involvement in G-protein-dependent lymphocyte recruitment into the central nervous system during experimental autoimmune encephalomyelitis, Eur. J. Immunol., 2002, vol. 32, pp. 2133-2144.

Ferrero et al. CD14+ CD34+ Peripheral Blood Mononuclear Cells Migrate Across Endothelium and Give Rise to Immunostimulatory Dendritic Cells. J. Immunol. 160:2675-2683 (1998).

International Search Report—PCT/US2007/083795 dated May 28, 2008.

International Search Report—PCT/US2008/056720 dated Jul. 29, 2008.

International Search Report—PCT/US08/70107 dated Mar. 13, 2009.

International Search Report—PCT/US06/048959 dated Jan. 13, 2009.

International Search Report—PCT/US07/014826 dated Dec. 30, 2008.

International Search Report—PCT/US08/69172 dated Mar. 25, 2009.

International Search Report—PCT/US07/013745 dated Apr. 18, 2008.

International Search Report—PCT/US05/14444 dated Mar. 21, 2008.

International Search Report—PCT/US06/43563 dated Nov. 29, 2007.

International Search Report—PCT/US06/43712 dated Aug. 8, 2007.

International Search Report—PCT/US07/006532 dated Dec. 8, 2008.

International Search Report—PCT/US07/006571 dated Sep. 21, 2007.

International Search Report—PCT/US07/013871 dated Mar. 3, 2008.

International Search Report—PCT/US06/049128 dated Jun. 12, 2007.

Printout of web page—Dynal (Norway): http://www.invitrogen.com/, printed Feb. 17, 2006.

Printout of web page—Agowa GMBH (Germany): http://agowade/contentsframes/magneticseparation/particle.html, printed Feb. 17, 2006.

Printout of web page—http://www.xcyte.com, printed Feb. 17, 2006.

Printout of web page—Protocol for anti-CD3 Activation of T-Cells from E-Bioscience (San Diego, CA): http://www.ebioscience..com/ebioscience/appls/AC145.htm, printed Feb. 17, 2006.

ARTIFICIAL TISSUE CONSTRUCTS COMPRISING ALVEOLAR CELLS AND METHODS FOR USING THE SAME

CROSS REFERENCE TO RELATED CASES

This application is a divisional of U.S. application Ser. No. 12/173,921, filed Jul. 16, 2008, which application claims the benefit of U.S. Provisional Application Ser. No. 60/949,944, filed Jul. 16, 2007, which are incorporated by reference herein in their entirety.

FIELD OF THE INVENTION

The present invention comprises artificial or man-made models of mammalian lung tissue and methods of using the same. The artificial tissue constructs of the present invention are functionally equivalent to in vitro lung tissue scaffolds that enable reliable and predictable modeling of human immunophysiological responses to particular conditions, environments and/or factors. The artificial tissue constructs can serve as novel platforms for the study of lung diseases (e.g., interstitial lung diseases, fibrosis, influenza, RSV, tuberculosis, anthrax, allergies), smoke- and smoking-related diseases, and the effects of particulate inhalation. The artificial tissue constructs of the present invention provide a structural basis for two components of alveolar tissue, namely an epithelial cell layer and an endothelial cell layer. These layers include appropriate cells, cytokines, growth factors, and extracellular matrix (ECM) materials. Methods are also provided that enable production of biocompatible, cellular, heterogeneous engineered tissue constructs (ETCs) that mimic the bronchoalveolar regions and alveolar sacs of mammalian lung tissue.

BACKGROUND OF THE INVENTION

One fifth of global mortality has been reported to be due to infectious disease. Within this, respiratory diseases alone account for about four million deaths per year (Girard et al. (2005) Vaccine 23, 5708-24). However, because of the expense of development, coupled with uncertainty regarding efficacy, only about 2% of the global pharmaceutical budget is allocated to development of new prophylactic vaccines (Kiney & Girard (2005) Vaccine 23, 5705-7). Given the scope of the worldwide health problems caused by known and emerging infectious diseases, and additionally, the potential of novel biological warfare pathogens, it is important that novel strategies of rapid vaccine evaluation be developed and implemented.

Lung Structure and Function

The mammalian lung is an organ within the thorax where passive diffusion of oxygen and carbon dioxide occur across a thin, two-cell-thick tissue. Normal lung function is to exchange oxygen from the air with carbon dioxide in the blood. Only two cell layers are interposed between the air and the blood, with a small amount of ECM serving as a scaffold.

The respiratory mucosa is the largest organ system directly open to the outside environment, with a surface area of 60-80 m$^2$. It serves as a point of entry for nutrient gases, along with microorganisms and particulate antigens that can trigger a multitude of respiratory immune responses. The first and the last point of contact occur at the nasopharynx and the alveolar regions of the lung, respectively.

The alveolus is the site where gaseous exchange occurs between the alveolar type I cells (respiratory epithelial cells), alveolar type II cells, and the vascular endothelial cells of the surrounding capillaries. These two cell layers prevent the direct mixing of air and blood, yet provide throughout the lung alveoli a massive surface area for gaseous exchange to occur. In an adult human, this surface area is about 60 m$^2$ during full expiration and about 80 m$^2$ during full inspiration.

Many pathophysiological conditions result in the direct increase or reduction of pulmonary mass, leading to a decrease in gaseous exchange. Non-malignant and malignant primary and metastatic lung tumors are principal reasons for permanent decreases in pulmonary function. Other causes of decreased pulmonary function include viral and bacterial pneumonias, trauma, fibrosis, and idiopathic disease.

The alveoli are tiny air sacs, the walls of which are covered with capillaries across which oxygen and carbon dioxide readily diffuse and are transferred into and out from the blood, respectively. This exchange is essential to survival and is the key function of the lungs.

The alveolus is a site where only two cell layers are interposed between the air and the blood, with a small amount of ECM serving as a membranous scaffold. Gaseous exchange occurs across the alveolar wall, comprising alveolar type I and type II cells (squamous respiratory epithelial cells) and the vascular endothelial cells of the surrounding capillaries.

Alveoli have fragile, thin walls, which are easily damaged. Breakage of these walls makes the oxygen-carbon dioxide diffusion much less efficient. The bronchial tree distributes the air throughout the lung to the individual alveoli. Once damaged, the bronchioles tend to collapse, trapping stale air in the isolated sacs and not letting fresh air in, leading to atelectasis.

Emphysema permanently enlarges and irreversibly damages the alveoli. It damages the ends and walls of the smallest bronchioles (the tiny breathing tubes that branch off from the trachea and bronchi), and diminishes pulmonary elasticity.

As alveoli and bronchial tubes are destroyed in pathophysiological conditions, progressively more air is required to provide the same amount of oxygen to the blood via the parts of the lung that are still functioning. This need for more air eventually leads to lung over-inflation. As the lung over-expands, it gradually enlarges, completely filling the maximum thoracic cage volume and causing a sense of shortness of breath. Because the lung can no longer expand or contract as completely as before, stale air left in the lung is never completely replaced with fresh air, resulting in poor gas exchange. The combination of a larger, less elastic lung and damaged, non-functioning tissue means that the air flow out of the lung is much slower, resulting in the feeling of an obstructed airway.

Many lung diseases that cause a narrowing of the respiratory airways (e.g., chronic bronchitis, asthma) can contribute to the onset of emphysema, but smoking is a common cause. In addition to the irreversible damage smoking causes to lung tissue, it causes inflammation of the lungs, which resolves only when smoking stops. Smoking also stresses the natural antioxidant defense system of the lung, allowing free radicals to damage lung tissue at the cellular level.

Additionally, irritants contained in tobacco smoke tend to inhibit activity of the cilia of the airways. These cilia ordinarily function to expel foreign matter and mucus from the lung. Without their activity, it becomes difficult or impossible to cough up the mucus that accompanies pneumonia and other lung infections. Cigarette smoke can temporarily paralyze the cilia. Smoking-induced emphysema usually becomes apparent after age 50.

The deposition of an inhaled particle in the lung has been linked to its size. For example, the upper respiratory mucosa is the first anatomic barrier where particles from ~5 to ~10 μm are deposited, while ~0.2 to ~2-μm sized particles are deposited in the lower mucosal alveolar region.

At the molecular level, the initial responses to such foreign particles include opsonizing agents (e.g., collectins), activation of cytochrome P450s, complement, lysozymes, anti-bacterial peptides (e.g., defensins), mannose-binding proteins, and interferons. Phagocytic cells activated at primary antigen deposition sites include alveolar macrophages and natural killer (NK) cells, which have the ability to recognize and neutralize infected cells, through recognition of bacterial and viral features. The adaptive responses trigger T and B lymphocytes that build immunological memory to subsequent challenges. This process is primarily regulated by antigen-presenting cells (APCs), such as macrophages, dendritic cells (DCs), and Type II epithelial cells. The T cell receptor (TCR) on the surface of the T lymphocyte is only activated by sensing major histocompatibility complex (MHC) molecules containing processed antigenic peptides on the surface of APCs. T cell responses are dependent on cytokines produced and functional effects after encountering antigen-specific T cells.

Respiratory epithelial cells have been shown to be responsive to lipopolysaccharides (Koyama et al. (1991) *J. Immunol.* 147, 4293-301; Diamond & Bevins (1994) *Chest* 105(3 Suppl), 51S-52S), muramyl dipeptides (Lopez-Boado et al. (2000) *J. Cell Biol.* 148, 1305-15; Diamond et al. (2000) *Infect Immun.* 2000 January; 68(1):113-9; Bevins (2003) *Contrib. Microbiol.* 10, 106-48), and lipoteichoic syncytial acid (Wagner et al. (1999) *Am. J. Respir. Cell Mol. Biol.* 20, 769-76; Diamond et al. (2000) *Infect Immun.* 2000 January; 68(1):113-9). They express Toll-like receptors (Holgate (2007) *Trends Immunol.* 28, 248-51; Bals & Hiemstra (2004) *Eur. Respir. J.* 23, 327-33; Becker et al. (2000) *J. Biol. Chem.* 275, 29731-6), TNF receptors (Levine (1995) *J. Investig. Med.* 43, 241-9; Nettesheim & Bader (1996) *Toxicol. Lett.* 88, 35-7), and demonstrate up-regulation of host defense genes, such as like MUC2, MUC5C, hBD2, and LL37/CAP18 (Becker et al. (2000) *J. Biol. Chem.* 275, 29731-6; Agerberth et al. (1999) *Am. J. Respir. Crit. Care. Med.* 160, 283-90; Bartman et al. (1998) *J. Pathol.* 186, 398-405; Yoon & Park (1998) *Rhinology* 36, 146-52; Dohrman et al. (1998) *Biochim. Biophys. Acta* 1406, 251-9; Li et al. (1997a) *J. Pathol.* 181, 305-10; Li et al. (1997b) *Proc. Natl. Acad. Sci. USA* 94, 967-72). Respiratory epithelium also produces interleukins (IL-1, IL-5, IL-6, IL-8), RANTES (regulated upon activation, normal T cell-expressed, and secreted), endothelin, granulocyte-monocyte colony stimulating factor (GM-CSF), transforming growth factor beta (TGF-β), interferon-γ-induced protein (IP-10), interferon-inducible T-cell α-chemoattractant (I-TAC), and γ-interferon-inducible T cell chemoattractant (Chung (2006) *Curr. Drug Targets* 7, 675-81; Prescott (2003) *J. Paediatr. Child Health* 39, 575-9; Holt & Stumbles (2000) *J. Allergy Clin. Immunol.* 105, 421-429).

As part of the adaptive immune response, memory T cells are constantly circulating through the lung parenchyma including alveolar spaces via well characterized lymphocyte homing mechanisms (Wardlaw et al. (2008) *Clin. Exp. Allergy* 35, 4-7). As the lung is considered a tertiary lymphoid organ (Grigg & Riedler (2000) *Am. J. Respir. Crit. Care* 162, 52-5), it contains large numbers of memory T cells in all compartments of the respiratory tract, with the largest number in the lung, migrating in through the post capillary venules under low hydrodynamic pressures. These memory T cells migrate specifically to the organ of their cognate antigen initiation. Much fewer naïve T cells enter the lung as age increases and only respond to newly seen antigens. These naïve T cells must enter the lung alveolar parenchyma via high endothelial venules under higher vascular pressures and faster flow. Unregulated T cell emigration into alveolar spaces and respiratory parenchyma may be a key factor for the formation of asthma (Bedoff et al. (2008) *Annu. Rev. Immunol.* 26, 205-32).

Respiratory Delivery Route

Advances in respiratory mucosal delivery have been driven by the non-invasive, highly absorptive properties of the respiratory route. Compared with the oral route, respiratory delivery offers a lack of digestive enzymes or mechanical forces, along with thin walls and a highly absorptive vascularized surface area for improved systemic delivery.

For vaccine or drug delivery, nebulizers and powder inhalers allow deposition of therapeutics in specific sites of the lung (Byron (2004) *Proc. Am. Thorac. Soc.* 1, 321-8; Laube (2005) *Respir. Care* 50, 1161-76). The potential for aerosolized vaccine delivery for influenza and measles, in addition to delivery of peptides and small molecule drugs has been explored with some success in asthma, chronic obstructive pulmonary disease (COPD), migraine, and diabetes-related therapeutics (Laube (2005) *Respir. Care* 50, 1161-76; Kennedy (1991) *Drugs* 42, 213-27; Illum (2002) *Drug Discov. Today* 7, 1184-9; Sullivan et al. (2006) *Expert Opin. Drug Deliv.* 3, 87-95). A prominent FDA-approved aerosolized vaccine is FluMist® vaccine, for seasonal flu. However, our limited understanding of the mechanistic details of the respiratory drug delivery has hampered the development of aerosolized therapeutics.

Other Respiratory Immunology/Toxicology Models: In Vivo and In Vitro Approaches

Since the 1970s there has been interest in developing in vivo respiratory models to study human immunology (e.g., Chowhan & Amaro (1976) *J. Pharm. Sci.* 65, 1669-72; Torkelson et al. (1976) *Am. Ind. Hyg. Assoc. J.* 37, 697-705; Belshe et al. (1977) *J. Med. Virol.* 1, 157-62; Saffiotti (1978) *Environ. Health Perspect.* 22, 107-13; Schanker (1978) *Biochem. Pharmacol.* 27, 381-5). Previous in vitro lung models included those based on the Transwell™ cell culture permeable support device or similar construct, comprising an endothelial cell layer, an epithelial cell layer, and an artificial microporous membrane, having pores therein, disposed between and in direct contact with the endothelial cell layer and the epithelial cell layer such that the membrane has an endothelial side and an epithelial side (see, e.g., U.S. Pat. No. 5,750,329; Weppler et al. (2006) *Exp. Lung Res.* 32, 455-82; Birkness et al. (1995) *Infect. Immun.* 63, 402-9; Birkness et al. (1999) *Infect. Immun.* 67, 653-658).

U.S. Pat. No. 5,750,329 describes a method for constructing an artificial lung system, comprising placing an artificial microporous membrane, having pores therein, into a vessel having a bottom and supporting the membrane a distance from the bottom of the vessel to create an upper and lower chamber in the vessel such that the membrane has an endothelial side facing into the lower chamber of the vessel and an opposite epithelial side facing into the upper chamber of the vessel; placing endothelial cells into the upper chamber of the vessel under conditions such that the endothelial cells form a confluent layer of cells on the epithelial side of the membrane; and placing alveolar epithelial cells into the upper chamber of the vessel under conditions such that the endothelial cells migrate through the pores in the membrane and attach to the endothelial side of the membrane to form a confluent layer of the endothelial cells on the endothelial side of the membrane in the lower chamber and the alveolar epithelial cells form a confluent layer of the epithelial cells on the epithelial side of the membrane in the upper chamber.

While in vivo animal models have been developed, variations in animal size, species, and differences in therapeutic distribution have resulted in inconsistencies in reported findings by various research groups using such models. Most in vivo models require destructive means for animal dosing using test compounds and vaccines, and blood and tissue isolation that also depend on animal handling/surgical protocols that are under scrutiny (Schanker & Hemberger (1984) *Pharmacology* 28, 47-50; Schanker & Hemberger (1983) *Biochem. Pharmacol.* 32, 2599-601; Schanker et al. (1986a) *Pharmacology* 32, 176-80; Schanker et al. (1986b) *Drug Metab. Dispos.* 14, 79-88; Schanker (1978) *Biochem. Pharmacol.* 27, 381-5; Hemberger & Schanker (1983a) *Drug Metab. Dispos.* 11, 73-4; Hemberger & Schanker (1983b) *Drug Metab. Dispos.* 11, 615-6; Brown & Schanker (1983a) *Drug Metab. Dispos.* 11, 355-60; Brown & Schanker L S (1983b) *Drug Metab. Dispos.* 11, 392-3; Lin & Schanker (1983a) *Drug Metab. Dispos.* 11, 75-6; Lin & Schanker (1983b) *Drug Metab. Dispos.* 11, 273-4; Mobley & Hochhaus (2001) *Drug Discov. Today* 6, 367-375, Widdicombe (1997) *J. Appl. Physiol.* 82, 3-12; Flecknell (2002) *ALTER* 19, 73-8; Abbott (2005 *Nature* 438, 144-6). Generally, the cost and time required for in vivo animal models along with physiological variations in the selected animal and human species (Li et al. (2007) *Exp. Lung Res.* 33, 227-44; Cao et al. (2007) *Toxicol. Lett.* 171, 126-37; Denham et al. (2007) *Am. J. Physiol. Lung Cell. Mol. Physiol.* 292, L1241-7; Carter et al. (2006) *J. Occup. Environ. Med.* 48, 1265-78) makes them less attractive than in vitro models for many purposes.

Compared with in vivo approaches, in vitro models are considered more humane, cost effective, are generally simpler to execute, and can use more physiologically relevant human cells. Various approaches have been adopted to develop in vitro respiratory system models using epithelial cell lines. However, the intrinsic differences between the functionality of these cell lines and native primary cells make these systems less than ideal. Several lung cell lines have been reported, including carcinoma-derived epithelial cell lines, such as A549 (alveolar), Calu-1, Calu-3, Calu-6, H441, HBE1, and A427. Normal tissue-derived transformed cell lines include 16HBE14o- (bronchial), 9HTE16o- (tracheal), 1HAEo- (tracheobronchial), BEAS-2B (bronchial), and CF/T43 (nasal). However, undesirable changes in cell line characteristics over passage culture have been reported, such as morphology, growth rates, protein expression, permeability, and signaling (ATCC Technical Bulletin no. 7, Passage number effects on cell lines. 2007 1-3; Esquenet et al. (1997) *J. Steroid Biochem. Mol. Biol.* 62, 391-9; Briske-Anderson et al. (1997) *Proc. Soc. Exp. Biol. Med.* 214, 248-57; Chang-Liu & Woloschak (1997) *Cancer Lett.* 113, 77-86; Yu et al. (1997) *Pharm. Res.* 14, 757-62, Sambuy et al. (2005) *Cell Biol. Toxicol.* 21, 1-26; Wenger et al. (2004) *Biosci. Rep.* 24, 631-9).

Such intrinsic differences can also be of concern when developing in vitro screening systems for therapeutics and pathogens. The need for highly functional primary lung epithelial cells has led to development of a number of primary cell isolation methods for mouse (Corti et al. (1996)*Am. J. Respir. Cell Mol. Biol.* 14, 309-15), rat (Goodman & Crandall (1982) *Am. J. Physiol.* 243, C96-100; Cheek et al. (1989) *Exp. Cell Res.* 184, 375-87) rabbit (Shen et al. (1999) *Pharm. Res.* 16, 1280-7), pig (Steimer et al. (2006) *Pharm. Res.* 23, 2078-93), and human lung tissue (Bur et al. (2006) *Eur. J. Pharm. Sci.* 28, 196-203; Elbert et al. (1999) *Pharm. Res.* 16, 601-8). However, differences between tissue responses between species have been noted, a possible drawback to using primary animal lung cells (Denham et al. (2007) *Am. J. Physiol. Lung Cell. Mol. Physiol.* 292, L1241-7; Carter et al. (2006) *J. Occup. Environ. Med.* 48, 1265-78).

Viral pathogens that cause respiratory disease include common flu or influenza (A or B; Orthomyxoviridae family), respiratory syncytial virus, human parainfluenza viruses (HPIVs; paramyxovirus family), metapneumovirus (hMPV; family Paramyxoviridae), adenoviruses, rhinoviruses, parainfluenza viruses, coronaviruses, coxsackievirus, and herpes simplex virus. Respiratory disease bacterial pathogens include *Yersinia pestis, Bacillus anthracis, Escherichia coli, Francisella tularensis, Staphylococcus aureus* Group A beta-hemolytic streptococci (GABHS), group C beta-hemolytic streptococci, *Corynebacterium diphtherias, Neisseria gonorrhoeae, Arcanobacterium haemolyticum, Chlamydia pneumoniae, Mycoplasma pneumoniae, Streptococcus pneumoniae, Haemophilus influenzae, Moraxella catarrhalis, Bordetella pertussis,* and *Bordetella parapertussis.*

There is a continuing need for a predictive, reproducible in vitro model system based on lung immunophysiology and function that would enable the study of a broad spectrum of respiratory disease pathogenesis and associated therapies. There is also a continuing need for in vitro immunological approaches for accurately predicting human immunological responses. The artificial tissue constructs of the present invention, with their use of three-dimensional (3D) tissue engineering and advanced cell biology, combined with modern bio-fabrication and bioreactor techniques, provide such a model system.

BRIEF DESCRIPTION OF THE INVENTION

The present invention comprises artificial tissue constructs comprising two layers of cells, wherein one layer of cells is positioned atop the other layer of cells, and wherein one of the layers of cells comprises alveolar primary epithelial cells and the other layer of cells comprising alveolar primary endothelial cells. The present invention also comprises methods of determining whether a test compound has immunological activity, comprising culturing an artificial tissue construct of the present invention in the presence of a test compound, and determining the effect the test compound has on an immunological activity of the artificial tissue construct. Immunological activities of the artificial tissue construct include immunoglobulin generation, chemokine generation and cytokine generation. The present invention further provides methods for preparing the artificial tissue constructs of the present invention.

The present invention also provides methods of preparing heterogeneous tissue constructs, comprising cells on the surfaces of a biocompatible membrane that mimic a vascular endothelium and a respiratory epithelium. In preferred embodiments the biocompatible membrane is selected from the group consisting of extracellular matrix, collagen, laminin, proteoglycan, vitronectin, fibronectin, poly-D-lysine and polysaccharide.

In other embodiments, other biocompatible membrane can be used to create an alveolar model. Additionally, the ECM structure can comprise different bio-material formulations, thicknesses, porosities, and cross-linking agents.

The artificial tissue constructs of the present invention can be used as part of in vitro diagnostic immunological methods for testing the effects of, for example, therapeutics, vaccines, particulates, and respiratory disease pathogens in the upper and lower airways. Using artificial tissue constructs of the present invention, comprising primary human cells, correlative responses can be determined from clinical studies and the supporting literature.

By increasing the accuracy of the artificial tissue constructs used in pre-clinical vaccine testing, it is possible to accelerate the rate of drug testing, increase the probability that any particular drug candidate will be successful in human trials, and augment the collection of more predictive data that will aid in pre-clinical design and formulation of therapeutics.

An embodiment of the present invention comprises an engineered 3D artificial tissue construct that mimics respiratory immunological function, and is superior to 2D cell representations and more relevant than animal models in assessing human respiratory immune responses.

Cell-based in vitro respiratory mucosal models for immunological evaluation have been under-used in the past because of limitations in maintaining primary cell function and the disparity of responses of intrinsically different cell lines. Embodiments of the present invention include the fabrication and functional testing of in vitro grown artificial tissue constructs, comprising primary human epithelial and endothelial cells from alveolar regions, that can be used to study the effects of and faithfully mimic the responses to, for example, airborne pathogens and human respiratory immunology. Variations in the thickness of the interposed extracellular matrix along with differing epithelial and submucosal cell types, will reproduce the different areas in the lung.

Historically, most in vitro models have used single or multiple layers of epithelial cells. The bilayer artificial tissue constructs of the present invention comprise an epithelium and an endothelium, representing the epithelial mucosa and the local tissue microvasculature. Autologous blood cells can be used to mimic the natural environment.

Embodiment of the present invention addresses the disadvantages in using animal models, because of physiological differences. The artificial tissue constructs of the present invention comprise native human cells of appropriate phenotypes from the alveolar regions.

The artificial tissue constructs of the present invention can be used to predict human physiological/immunological responses in an in vitro setting. Further, they can be used to assess responses to viral (e.g., influenza, respiratory syncytial virus) and bacterial (e.g., $E.\ coli$ and $S.\ aureus$) exposure. The effects of, for example, immunosuppressive corticosteroid hormones (e.g., dexamethasone, hydrocortisone, alclometasone, amcinonide, beclometasone, betamethasone, budesonide, ciclesonide, clobetasol, clobetasone, clocortolone, cloprednol, cortivazol, deflazacort, deoxycorticosterone, desonide, desoximetasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, ulobetasol) and environmental irritants (e.g., diesel particles) and potentially carcinogenic polycyclic hydrocarbons (e.g., 3-methylcholantherene, $\beta$-nitrophenol) can also be evaluated.

Embodiments of the present invention comprise bilayer alveolar mucosal models, comprising primary alveolar epithelial and endothelial cells, optionally cultured with extracellular matrix proteins, that promote a desirable type-II epithelial cell phenotype and biological function. To make the artificial tissue constructs, both lung and other tissue and cell samples are preferably from the same person or animal.

In preferred embodiments of the present invention, the bilayer artificial tissue constructs comprise human primary alveolar epithelial and human endothelial cells cultured with extracellular matrix proteins that promote a desirable type-II epithelial cell phenotype and biological function. To make the constructs, both lung and other tissue and cell samples are preferably from the same person.

The bilayer alveolar artificial tissue constructs of the present invention comprise a confluent endothelium and epithelium. The epithelium comprises both type I and type II epithelial cells. Vesicle formation and cycling also occur in the constructs.

We have demonstrated that the type II cells are pseudo antigen-presenting cells. The artificial tissue constructs mount immunological responses to bacterial stimulants and hormonal immunosuppressants. The functioning of the artificial tissue construct was also assessed by cytochrome P450 activity. Collectively, these data demonstrate that the tissue-engineered in vitro artificial tissue constructs of the present invention are functional.

In one embodiment the present invention includes an artificial tissue construct comprising: (a) a first cellular layer comprising alveolar primary epithelial cells and having a first face and a second face, and (b) a second cellular layer comprising alveolar primary endothelial cells, wherein the second layer is positioned on the first face or the second face of the first layer.

In preferred versions of this embodiment the alveolar primary epithelial cells are human cells, or the alveolar primary endothelial cells are human cells, or both the alveolar primary epithelial cells and the alveolar primary endothelial cells are human cells.

In versions of this embodiment where both the alveolar primary epithelial cells and the alveolar primary endothelial cells are human cells, both the alveolar primary epithelial cells and the alveolar primary endothelial cells are from the same human.

In other preferred versions of this embodiment the artificial tissue construct further comprise primary alveolar macrophages, preferably wherein the primary alveolar macrophages are interspersed among the alveolar primary epithelial cells and/or the alveolar primary endothelial cells. The primary alveolar macrophages may also be interspersed among the alveolar primary epithelial cells and the alveolar primary endothelial cells, and be positioned between the first cellular layer and the second cellular layer. The artificial tissue construct may also comprise blood cells, preferably white blood cells.

In this embodiment of the invention a biocompatible membrane may be positioned between the first cellular layer and the second cellular layer of the artificial tissue construct. The biocompatible membrane may be selected from the group consisting of basement membrane, extracellular matrix, collagen, laminin, proteoglycan, vitronectin, fibronectin, poly-D-lysine and polysaccharide. In a preferred embodiment the biocompatible membrane is an extracellular matrix comprising laminin and collagen. In equally preferred embodiments the first cellular layer and the second cellular layer are in direct contact.

In a second embodiment the present invention is directed to methods of determining whether a test compound has an immunological activity, wherein the method comprises:

(a) culturing an artificial tissue construct of the present invention with a test compound, (b) assaying an immunological activity of the artificial tissue construct of (a), and (c) comparing the immunological activity assayed in (b) to the immunological activity assayed for the artificial tissue construct of claim 1 cultured in the absence of the test compound, wherein when there is a difference in the immunological activity of the artificial tissue construct in the presence of the test compound compared to an absence of the test compound, the test compound is determined to have an immunological activity.

In this embodiment, the immunological activity may be selected from the group consisting of immunoglobulin generation, chemokine generation, and cytokine generation.

Also in this embodiment, the test compound may be selected from the group consisting of cigarette smoke, cigarette smoke particulates, an aerosol, a therapeutic agent, a biological compound, a vaccine, a respiratory bacterial disease pathogen, a respiratory disease viral pathogen, an environmental irritant, a diesel particle, a cosmetic ingredient and a polycyclic hydrocarbon.

In an embodiment where the test compound is a vaccine, the vaccine may be an influenza vaccine or a measles vaccine.

In an embodiment where the test compound is a respiratory disease bacterial pathogen, the respiratory disease bacterial pathogen may be selected from the group consisting of *Y. pestis, Bacillus anthracis, E. coli, Francisella tularensis, S. aureus*, Group A beta-hemolytic streptococci (GABHS), group C beta-hemolytic streptococci, *Corynebacterium diphtherias, Neisseria gonorrhoeae, Arcanobacterium haemolyticum, Chlamydia pneumoniae, Mycoplasma pneumoniae, Streptococcus pneumoniae, Haemophilus influenzae, Moraxella catarrhalis, Bordetella pertussis,* and *B. parapertussis*.

In an embodiment where the test compound is a respiratory disease viral pathogen, the respiratory disease viral pathogen may be selected from the group consisting of common flu, influenza A, influenza B, respiratory syncytial virus (RSV), adenovirus, parainfluenza virus, human parainfluenza virus (HPIV), metapneumovirus (hMPV), rhinovirus, coronavirus, coxsackievirus and herpes simplex virus.

In an embodiment where the test compound is a therapeutic agent, the therapeutic agent may be an immunosuppressive drug or a small drug molecule.

In an embodiment where the test compound is an immunosuppressive drug, the immunosuppressive drug may be a corticosteroid.

In an embodiment where the test compound is an immunosuppressive corticosteroid hormone, the immunosuppressive corticosteroid hormone may be selected from the group consisting of alclometasone, amcinonide, beclometasone, betamethasone, budesonide, ciclesonide, clobetasol, clobetasone, clocortolone, cloprednol, cortivazol, deflazacort, deoxycorticosterone, desonide, desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, and ulobetasol.

In an embodiment where the test compound is an environmental irritant, the environmental irritant may be an environmental chemical irritant.

In an embodiment where the test compound is a polycyclic hydrocarbon, the polycyclic hydrocarbon may be 3-methylcholantherene or β-nitrophenol.

In an embodiment where the test compound is a biological compound, the biological compound may be selected from the group consisting of a peptide, a polypeptide, an antibody, a monoclonal antibody, an oligonucleic acid molecule, a polynucleic acid molecule, a saccharide, and a polysaccharide.

BRIEF DESCRIPTION OF THE FIGURES

FIG. 6A shows production levels of IL-6, IL-8, MCP-1, RANTES, and IP-10. FIG. 6B shows production levels of IL-12 (p40), IL-15, GM-CSF, IFN-γ, eotaxin and MIP-1α

FIG. 7A shows production levels of IL-6, IL-8, MCP-1, RANTES, and IP-10. FIG. 7B shows production levels of IL-12 (p40), IL-15, GM-CSF, IFNγ, Eotaxin and MIP-α.

DETAILED DESCRIPTION OF THE INVENTION

Figure 1:
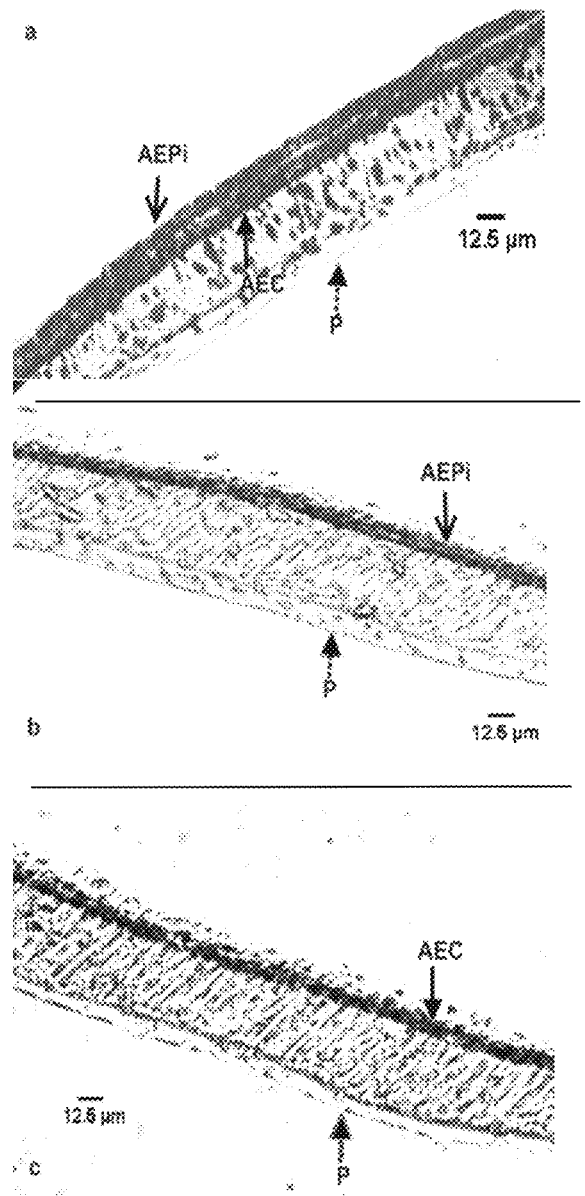
FIG. 1 show immunohistochemical staining of alveolar mucosal constructs. Panel a) is a bilayer structure showing a distinctive epithelium (AEPi) on top of endothelium (AEC). Panel b) shows an epithelium. Panel c) shows an endothelium. In each panel P=the porous Transwell surface.

The present invention is directed to artificial tissue constructs comprising two layers of cells, wherein one layer of cells is positioned atop the other layer of cells, and wherein one of the layers of cells comprises alveolar primary epithelial cells and the other layer of cells comprising alveolar primary endothelial cells. The present invention is also directed to methods of determining whether a test compound has immunological activity, comprising culturing an artificial tissue construct of the present invention in the presence of a test compound, and determining the effect the test compound has on an immunological activity of the artificial tissue construct. Immunological activities of the artificial tissue construct include immunoglobulin generation, chemokine generation and cytokine generation. The present invention further provides methods for preparing the artificial tissue constructs of the present invention.

Artificial Tissue Constructs

The artificial tissue constructs of the present invention are tissue constructs comprised primary of cells derived from respiratory tissue that may be used to test and screen compounds in vitro for the potential effects the compounds might have on immunological activities of lung tissues in vivo.

At the most basic level, the artificial tissue constructs of the present invention comprise two layers of cells (cellular layers), wherein one layer of cells is on top of and in contact with the other layer of cells, for example, in the form of two coins that are stacked, one atop the other. One of the layers of cells (at times referred to herein as a "first cellular layer" for sake of convenience and not to denote any limitations regarding the placement of the layer in the constructs of the present invention) is comprised primarily of pulmonary alveolar respiratory epithelial cells, preferably obtained from the alveolar regions of lung tissue. The pulmonary alveolar respiratory epithelial cells may be Type I cells, Type II cells or a mixture of Type I cells and Type II cells. The skilled artisan will understand that such cells are the epithelial cells of the alveoli that are in direct contact with air that enters the lungs of a mammal. The skilled artisan will understand that based on the particular use to which the artificial tissue constructs will be put, other types of respiratory epithelial cells may be used.

The second of the layers of cells (at times referred herein to as a "second cellular layer" for sake of convenience and not to denote any limitations regarding the placement of the layer in the constructs of the present invention) is comprised primarily of respiratory endothelial cells, preferably vascular endothelial cells obtained from the alveolar regions of lung tissue. The skilled artisan will understand that such cells are the endothelial cells of capillaries in contact with the alveoli that are in direct contact with the blood of the capillaries. Thus, the artificial tissue constructs of the present invention mimic in structure the two cell layers that comprise mammalian alveoli.

The cells that make up the cellular layers are mammalian cells, including human, simian, mouse, rat, rabbit, guinea pig, horse, cow, sheep, goat, pig, dog and cat cells. Preferably the cells are human cells. The cells that comprise the constructs may come from a single individual mammal, such a one man, or come from more than one individual. When from more than one individual the cellular layers may be each comprises of cells from a different individual, or the cells comprising each layer may be from different individuals.

The cells that make up the layers may be obtained from existing cell cultures, or produced de novo by disassociating primary epithelial and endothelial cells from lung tissue and culturing such cells under appropriate conditions to form the cellular layers.

The artificial tissue constructs of the present invention also may comprise a biocompatible membrane that is positioned between the two layers of cells. Alternatively, both cellular layers may be positioned on top of the biocompatible membrane. Such biocompatible membranes may serve to maintain the layers of cells as discrete cellular layers in the contrast. The biocompatible membrane may also provide mechanical support for the constructions. The biocompatible membrane further provide a means for allowing selective passage between the two cellular layers and may thus be impermeable, semi-permeable or porous, thereby controlling the ability of fluids, gases, small molecules and cells to pass from one cellular layer to another. The biocompatible membrane may be any material that does not have a deleterious effect on the basic nature of the artificial tissue construct. Suitable examples of biocompatible membranes include materials comprising basement membrane, extracellular matrix, collagen, laminin, proteoglycans, vitronectin, fibronectin, poly-D-lysine and/or polysaccharides. When the biocompatible membrane comprise extracellular matrix it may be comprised of laminin and collagen.

The thickness of the biocompatible membrane will differ depending on the material that is being used and the composition of the cellular layers in the constructs. However, it is envisioned that the biocompatible membrane will range in size from less than about 200 nm to more than about 1 mm. In preferred embodiments the biocompatible membrane is about 0.5 nm to about 1 um.

The skilled artisan will understand that the constructs of the present invention may also comprise constructs where the first cellular layer and the second cellular layer are in direct contact.

The artificial tissue constructs of the present invention may be of varying sizes and shapes, and the skilled artisan will understand that there are few limitations on the three-dimensional structure of the constructs. Thus, the cellular layers may be of any shape, including round, oval, rectangular, triangular and square. The cellular layers may each of be a different shape or size, or of the same general shape or size. The cellular layers may be of different thicknesses, or have the same general thickness. It is convenient to consider each cellular layer as being a very flat structure, resembling the structure of a coin, that has a first face and a second face in opposition to each other (the "heads" and "tails" sides of a coin), as well as an narrow edge that encompasses the circumference of the layer. In preferred embodiments the two layers are position such that the face of one layer is positioned in parallel and against the face of the other layer, such as a stack of two coins mentioned above. However, as also indicated above the two layers may be in direct contact or separated by the biocompatible membrane. The two layers may be positioned entirely against each other or may be positioned with less than the entire layers being position against each other. The first cellular layer may be positioned on top of the second cellular layer, or the second cellular layer may be positioned on top of the first cellular layer.

The artificial tissue constructs of the present invention may be prepared, grown and maintained in any suitable tissue culture vessel that permits production, growth and maintenance of the constructs. Suitable vessels include Transwell™ cell culture permeable support devices and T-75 flasks.

The artificial tissue constructs of the present invention may be prepared by, for example, from autologous epithelial and endothelial cells that are isolated from normal human tissue biopsy samples by literature procedures. A tissue culture vessel (plate or flask, e.g., Transwell™ cell culture buckets or a T-75 flask) may be coated with fibronectin (5-50 mg/mL) and placed in an incubator at 37° C. prior to seeding with cells. Endothelial cells can be disassociated from lung tissue samples and added to the tissue culture vessel, for example, at a density of ~25,000-35,000 cells/well in a Transwell™ cell culture bucket. The cells can be cultured until approximate confluency is reached. Endothelial cells can then be disassociated from lung tissue samples and added to the tissue culture vessel containing the confluent endothelial cells, with seeding at a density of ~20,000-25,000 per well. The epithelial cells can be cultures in, for example, Media 199 (M199) and Dulbecco's minimum essential medium (DMEM). The resulting artificial tissue constructs of the present invention may be maintained by culturing them at 37° C. in 5% $CO_2$.

The artificial tissue constructs of the present invention may also comprise additional cell types in addition to the alveolar epithelial and vascular endothelial cells described above. For example, the constructs may further comprise primary alveolar macrophages. The primary alveolar macrophages may be interspersed with the first cellular layer, the second cellular layer, or both. The primary alveolar macrophages may also be within the biocompatible membrane. The skilled artisan will understand that primary alveolar macrophages will migrate within and to different regions of the construct, and within and between the cellular layers. The artificial tissue constructs may also contain one or more of the following cell types: red blood cells, white blood cells, including monocytes, T lymphocytes (including CD4+ and CD8+ T cells), B lymphocytes, and natural killer cells, The artificial tissue constructs of the present invention may also comprise additional components, including cytokines and growth factors.

The present invention is also directed to methods of determining whether a test compound has immunological activity, comprising culturing an artificial tissue construct of the present invention in the presence of a test compound, and determining the effect the test compound has on an immunological activity of the artificial tissue construct.

The test compounds assayed in these methods are any for which one wishes to determine the effect the compound has on an immunological activity of the lung of a mammal. It will be readily apparent to the skilled artisan that the test compounds will include those compounds which are suspected of causing a deleterious effect on lung tissue, such environmental pollutants and irritants, such as emissions and particulates contained therein from various manufacturing processes and facilities, power generating facilities and internal combustion engines, allergens; cigarette smoke and the particulates contained within cigarette smoke (such as nicotine, hydroquinone, and benzopyrene); a cosmetic ingredient; a polycyclic hydrocarbon (such as 3-methylcholantherene and β-nitrophenol); respiratory bacterial disease pathogens; and respiratory disease viral pathogens.

Allergens include antigenic compounds that may be inhaled, such as molds, ragweed, tree and grass pollens, pet dander, and house dust mites.

Respiratory disease bacterial pathogens include *Y. pestis, Bacillus anthracis, E. coli, Francisella tularensis, S. aureus*, Group A beta-hemolytic streptococci (GABHS), group C beta-hemolytic streptococci, *Corynebacterium diphtherias, Neisseria gonorrhoeae, Arcanobacterium haemolyticum, Chlamydia pneumoniae, Mycoplasma pneumoniae, Streptococcus pneumoniae, Haemophilus influenzae, Moraxella catarrhalis, Bordetella pertussis, B. parapertussis, M. pneumoniae* and *C. pneumoniae*. Respiratory disease viral pathogens include common flu, influenza A, influenza B, respiratory syncytial virus (RSV), adenovirus, parainfluenza virus, human parainfluenza virus (HPIV), metapneumovirus (hMPV), rhinovirus, coronavirus, coxsackievirus and herpes simplex virus.

Test compounds include compounds of a medical nature that might be used in the prevention and/or treatment of disease. Such compounds include aerosols and the components thereof that might be used as a carrier in the administration of a therapeutic agent, vaccine or other compound to a subject via the lungs, vaccines themselves (such as an influenza vaccine or a measles vaccine), therapeutic agents themselves (such as a small drug molecule or an immunosuppressive drug, e.g., an immunosuppressive corticosteroid hormone), and other biological compounds (such as a monoclonal antibody, a peptide, a polypeptide, an oligonucleic acid molecule, a polynucleic acid molecule, a saccharide, and a polysaccharide).

Immunosuppressive corticosteroid hormones include alclometasone, amcinonide, beclometasone, betamethasone, budesonide, ciclesonide, clobetasol, clobetasone, clocortolone, cloprednol, cortivazol, deflazacort, deoxycorticosterone, desonide, desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, and ulobetasol.

The immunological activities for which the test compounds may be assayed include all of the immunological activities that take place in the lungs of a mammal. Examples of immunological activity include up-regulation of host defense genes (including MUC2, MUC5C, hBD2, and LL37/CAP18), immunoglobulin generation, chemokine generation (such as interferon-inducible T-cell α-chemoattractant (I-TAC), and γ-interferon-inducible T cell chemoattractant), and cytokine generation (including interleukins (IL-1, IL-5, IL-6, IL-8), RANTES (regulated upon activation, normal T cell-expressed, and secreted), endothelin, granulocyte-monocyte colony stimulating factor (GM-CSF), transforming growth factor beta (TGF-β) and interferon-γ-induced protein (IP-10).

The effect a test compound has on a particular immunological activity of the constructs of the present invention will be determined in a somewhat different manner depending in the nature of the test compound, the composition of the artificial tissue construct and the particular immunological activity being assayed. However, the general method will be the same regardless of these variables and includes:

(a) culturing the artificial tissue construct with a test compound, (b) assaying a selected immunological activity of the artificial tissue construct, and (c) comparing the values determined in the assay to the values of the same assay performed using an artificial tissue construct with the same composition as in (a) but cultured in the absence of the test compound (or in the presence of a control). The difference between the values determined for the assay in the presence and absence of the test compound will provide specific information regarding the effect the test compound has on the immunological activity of the artificial tissue construct, which may be extrapolated to the potential effect the test compound will have on the immunological activity of the lung and lung tissue of a living mammal.

As indicated above, the particular assay used in the methods of the present invention will vary, primarily based on the particular immunological activity being assayed. For example, when the immunological activity being assayed is up-regulation of host defense genes, one might assay for RNA production (via northern blot analysis) or protein production (via a western blot analysis) corresponding to those genes known to be up-regulated in a host defense reaction. Similarly, where the immunological activity being assayed is immunoglobulin generation one might assay for immunoglobulin RNA production (via northern blot analysis) or protein production (via a western blot analysis).

Where the immunological activity being assayed is chemokine or cytokine generation, one might again assay for RNA production (via northern blot analysis) or protein production (via a western blot analysis) corresponding to particular chemokines or cytokines.

In the examples that follow, immunohistochemical staining of the bilayer constructs demonstrate the endothelial/epithelial bilayer structure of the artificial tissue constructs. The functionality of the epithelium was shown by vesicle cycling analysis of FM-143FX, tetanus toxoid and keyhole limpet hemocyanin across the mucosal construct. Experimental data generated with an artificial tissue construct of the present invention showed that it responded to chemical stimuli, such as immunosuppressant hormones (e.g., dexamethasone, hydrocortisone) and bacterial treatments (e.g., *S. aureus, E. coli*). Cytochrome P450 activity experiments also showed that the alveolar cells had significant P450 activity that can be quantified after induction by various irritants.

EXAMPLES

Example 1

Fabrication of Bilayer Artificial Tissue Constructs

In an embodiment of the present invention, artificial tissue constructs were prepared by creating a bilayer cellular structure on top of a collagen and laminin-coated porous plastic membrane. Primary cell isolations from normal human tissue biopsy samples were performed to isolate autologous epithelial and endothelial cells. The tissue was stored in preservation media for up to ~24 h before cell isolation. The cell isolation protocol was similar to that in previous reports (Bur et al. (2006) *Eur. J. Pharm. Sci.* 28, 196-203; Elbert et al. (1999) *Pharm. Res.* 16, 601-8). Enzyme-based tissue digestion was performed with elastase and trypsin, followed by IgG panning to isolate different cell populations.

Experiments were performed with a series of extracellular matrix proteins and chitosan, a natural polysaccharide, as examples. Specifically, collagen, fibronectin, laminin, Matrigel™ (a gelatinous protein mixture), collagen, and chitosan-blended extracellular matrix proteins were examined. Blended and cross-linked materials were cased into gels, porous scaffolds, and coatings to determine the effects of material microstructure on tissue generation in vitro. The gelled materials were prepared with collagen and collagen-blended fibronectin or laminin by controlling the pH of the protein solutions with buffers at controlled temperatures until the polymers formed a physical gel, based charge density. The porous scaffolds were prepared using chitosan-based materials with or without collagen and laminin. The porosity of the scaffold was controlled by adjusting the density of the polymer solutions, freezing the solution under controlled temperature conditions, and later lyophilizing the mixture.

In a preferred embodiment, the coatings were prepared by pouring the polymer solutions (collagen, including type 4 collagen, and laminin) on the porous support. The thin polymer coating was then aspirated off the support and the coated surfaces were allowed to air dry prior to cell seeding. Primary alveolar endothelial cells were cultured on top of the plastic membranes until they reached confluency. The alveolar epithelial cells were then seeded on top of the endothelial cells, to create an epithelium.

In a preferred embodiment of the present invention, the following protocol was used to generate artificial tissue constructs. Suitable materials can be purchased, for example, from the following suppliers: penicillin-streptomycin-glutamine (Sigma), Media199 (Invitrogen), Dulbecco's minimum essential medium (Invitrogen), fibronectin (BD Biosciences), ethanol (Sigma), collagen (Inamed), laminin (BD Biosciences), HTS-Transwell™ cell culture plates (Corning Life Sciences), trypsin-EDTA (Sigma), 1×PBS (Sigma), fetal bovine serum (Hyclone), human alveolar endothelial cells (ScienCell), and human alveolar epithelial cells (ScienCell).

For the endothelial cell culture, endothelial cell media was used. Media 199 (M199) stock solution containing 1% penicillin-streptomycin-glutamine was prepared, and was supplemented with 5-15% (v/v) fetal bovine serum. A tissue culture vessel (plate or flask) was coated with fibronectin (5-50 mg/mL) and placed in the incubator for ~1 h. Later, the fibronectin was removed and serum-containing media was added to the tissue culture vessel. For example a volume of 12 mL of 10% serum containing culture media was added to a T-75 flask coated with 5 mg/mL of fibronectin solution. A vial of human alveolar endothelial cells was thawed at 37° C. and the cell suspension was added to the coated tissue culture vessel. The flask was placed in the incubator and the media was changed ~24 h after cell seeding. The media was changed every ~48 h after the initial ~24-h incubation period until the cells reached ~90% confluency.

To subculture the cells, another fibronectin-coated vessel was prepared. PBS, tissue dissociation enzyme (like trypsin-EDTA), and serum-containing media were warmed to 37° C. The cells were rinsed with PBS and trypsin-EDTA solution was added. The detached cells (round morphology) were observed under a light microscope. Media containing 5-15% serum was then added to the cell suspension and then centrifuged (~1000 rpm, ~10 min). The supernatant was aspirated and the cell pellet was re-suspended in serum-containing media. The cells were counted and diluted as needed. The cells were then seeded in tissue culture vessels. For example, a seeding density of ~20,000-35,000 cells/well was used for the multi-well Transwell™ cell culture devices (0.33 cm$^2$).

For the epithelial cell culture, epithelial cell media was used. Media 199 (M199) and Dulbecco's minimum essential medium (DMEM) stock solutions containing 1% penicillin-streptomycin-glutamine were prepared. A 5-15% (v/v) serum-containing culture media was prepared in 50:50 solution of DMEM and M199. The tissue culture vessel was coated with fibronectin (5-50 mg/mL) and placed in an incubator (37° C.). After approximately 1 h, serum-containing tissue culture media was then added to the coated tissue culture vessel. For example, a volume of 12 mL of 10% serum containing culture media was added to a T-75 flask coated with 5 mg/mL of fibronectin solution. A vial of human alveolar epithelial cells was thawed at 37° C. and the cell suspension was added to the serum-containing media. The cells were cultured in an incubator and media was changed ~24 h after cell seeding. The media was changed every ~48 h after the initial ~24-h incubation period until the cells reached ~90% confluency.

To subculture the cells, another fibronectin-coated vessel was prepared, as described above. PBS, tissue dissociation enzyme (like trypsin-EDTA), and serum-containing media were warmed to 37° C. The cells were rinsed with PBS and Trypsin-EDTA solution was added. The detached cells (round morphology) were observed under a light microscope. 5-15% serum-containing media was then added to the cell suspension and then centrifuged (~1000 rpm, ~10 min). The supernatant was aspirated and the cell pellet was re-suspended in serum-containing media. The cells were counted and diluted as needed. The cells were then seeded in tissue culture vessels. For example, a seeding density of ~25,000-35,000 cells/well was used for the multi-well Transwell™ cell culture devices (0.33 cm$^2$).

In a preferred embodiment of the present invention, a mucosal construct was prepared on multi-well HTS-Transwell™ cell culture plates. The cell growth surface area of a Transwell™ cell culture bucket is 0.33 cm$^2$. The coating volumes and cell densities can be scaled, based on the cell growth surface area of the vessel or surface of interest.

HTS-Transwell™ cell culture plates (24-well) were coated with 0.1-1% (w/w) laminin and collagen solution: the dilutions were prepared in M199/DMEM. The plates were incubated at room temperature for ~1 h. The collagen/laminin solution was then aspirated off and ~75 μL of media was added to the coated membrane: ~300 μL of media was added to the bottom well. The plates were placed in the incubator overnight.

Human alveolar endothelial cells were added to the Transwell™ cell culture buckets, at a density of ~25,000-35,000 cells/well. The media was changed ~24 h after cell seeding and at ~48-h intervals for one week, by when the endothelial cells reached approximate confluency. Human alveolar epithelial cells were then added on top of the endothelial cells at a seeding density of ~20,000-25,000 per well.

In another embodiment, if a higher density of Type II alveolar epithelial cells was desired, then the confluent endothelial cell layer was coated with ~50 μL collagen-laminin solutions, as described above. The coating solution was then aspirated, and the cells were incubated with ~75 μL of serum-containing epithelial cell media for ~30 min. The media was then aspirated and epithelial cells were added on top of the coated endothelial cell layer, at a density of ~20,000-30,000 cells per well. The media was changed ~24 h after cell seeding and at ~48-h intervals for one week, by which time the endothelial cells had reached approximate confluency. It usually took ~2 to ~3 days for the epithelial cells to grow to approximate confluency.

Example 2

Characterization of the Constructs

Immunohistochemical staining of the mucosal construct was used to identify the presence and location of the epithelial and endothelial cells in the bilayer structure. Epithelial cells in the construct were identified by immunohistochemical staining of a number of alveolar cell-specific cytokeratins, including CK-1, 4, 5, 6, 8, 10, 13, 18, 19.

In the staining method formalin-fixed tissue was embedded in paraffin wax and sectioned at 5 μm. The paraffin wax was then dissolved with xylene and sections were blocked with ~10% goat serum. A primary cytokeratin antibody cocktail was then added, followed by the addition of the biotinylated secondary antibody. Streptavidin-peroxidase enzyme conjugate was then applied and aminoethyl carbazole (AEC) chromagen was later added to the sections. The samples were counterstained with hematoxylin and rinsed thoroughly with dH$_2$O and incubated until color developed. Light microscopy was used to image the cytokeratin-containing epithelial cells in the in vitro-grown mucosal constructs.

Alveolar endothelial cells in the mucosal construct were identified by Factor VIII staining, specific for endothelial cells. The formalin-fixed tissue samples were paraffin wax-embedded and sectioned at 5 μm for antibody staining. The tissue was then deparaffinized and blocked with 10% goat serum to reduce non-specific staining. Primary antibody was applied for 1 h at room temperature or incubated overnight at 4-6° C., followed by a biotinylated secondary antibody for 30 min. A streptavidin-peroxidase enzyme conjugate was then applied and aminoethyl carbazole (AEC) chromagen was later added. Light microscopy of the sections showed the red staining of Factor VIII on the endothelial cells. The tissue integrity of each cell monolayer was characterized by tight junction staining of ZO-1, E-cadherin, and occludin. Confocal microscopy was performed on the formalin-fixed epithelial and endothelial tissue.

Double staining of both alveolar epithelial and endothelia cells showed a clear bilayer structure of the mucosal construct on top of a porous plastic support (FIG. 1). The top layer of cells showed cytokeratin staining, characteristic of epithelial cells and the bottom cell layer showed Factor VIII staining, characteristic of endothelial cells. Individual staining of the epithelium and endothelium also showed a single layer of tissue per cell type. Tight junction staining of the endothelium and the epithelium showed a confluent cell layer.

Example 3

Type II Alveolar Epithelial Cell

After successfully expanding and co-culturing human epithelial and endothelial cells on laminin-coated membranes and porous scaffolds, cell morphology and activity was examined. In particular, the presence of Type II alveolar epithelial cells was studied. These cells participate in vivo in primary inflammatory and immune reactions in lung mucosa towards external contaminants and pathogens. Type II cells produce a lung surfactant substance that comprises lipoproteins and surfactant proteins able to bind polysaccharides of bacterial membranes, and enhance protective release of oxygen radicals by alveolar macrophages.

The morphology of Type I and Type II epithelial cells was examined by transmission electron microscopy of epoxy-embedded and microtome-sectioned samples of the mucosal tissue constructs of the present invention. Briefly, cultured epithelial cells were fixed with 2.5% gluteraldehyde and were later exposed to osmium tetroxide. Serial ethanol dehydration was then performed, followed by tissue infiltration of propylene oxide. The samples were then transitioned through propylene oxide and epoxy resin, followed by embedding in 100% epoxy resin. Epon 812 along with dodenyl succinic anhydride (DDSA), nadic methyl anhydride (NMA), and 2,4,6-tri(dimethylaminomethyl) phenol (DMP-30) were used to prepare the embedding polymer resin. The samples were sectioned at 100 nm using a Leica UltraCut™ Microtome. Sections were then stained with 2% uranyl acetate followed by a lead citrate treatment. The TEM used was a Hitachi H-7000™ transmission electron microscope.

Visualization of Type II cells with the FM143-FX fluorescent dye was based on exocytotic activity of the Type II cells. The amphiphilic fluorescent styryl dye FM143-FX, or (N-(3-triethylammoniumpropyl)-4-[dibutylaminostyryl] propidinium dibromide) is actually non-fluorescent in an aqueous environment, but becomes fluorescent when it comes in contact with lipid-containing plasma membranes and vesicles. Type II alveolar cells release vesicles filled with surfactant proteins and lipoproteins through fusion pores. Infiltration of the FM143-FX dye through these pores into the phospholipid-containing lamellar bodies (pre-formed vesicles) and plasma membranes results in bright red fluorescence. Two-week old constructs containing either alveolar epithelial or endothelial cells or a combination of both cell types were used for the cell transport studies. Tissue constructs were fixed with 4% paraformaldehyde and 5 µg/mL of FM143FX (Invitrogen) in HEPES-containing media was added to the treated constructs. Cells were visualized with an Olympus Fluoview FV300™ confocal laser scanning biological microscope. The mucosal tissue was visualized at various depths to locate the fluorescent FM143FX-containing vesicles.

Staining of epithelial cytokeratins was performed on formalin-fixed, non-embedded, non-sectioned epithelial/endothelial constructs, using an anti-pan cytokeratin immunohistochemical cocktail (Sigma-Aldrich) that contains monoclonal antibodies to human CK-1, 4, 5, 6, 8, 10, 13, 18, 19, that are alveolar epithelial tissue-specific. Apart from the primary monoclonal antibody, all reagents were from Invitrogen.

The tissue construct was fixed in neutral buffered formalin containing ~10% goat serum was used as a blocking solution. The primary antibody pan-cytokeratin cocktail was then added and samples were incubated at room temperature. Biotinylated secondary antibody was then added followed by a repeated incubation period. Streptavidin-peroxidase enzyme conjugate was then applied and aminoethyl carbazole (AEC) chromagen was later added to the constructs. The samples were then counterstained with hematoxylin and rinsed thoroughly with $dH_2O$ and incubated until color developed. Light microscopy was used to image the cytokeratin containing epithelial cells (purple) in the in vitro-grown mucosal constructs.

TE images of Type I and Type II cells revealed multiple lamellar bodies and vesicles filled with surfactant, which helped to discriminate Type I and Type II cells. These results show that the collagen- and laminin-containing scaffold materials did promote the growth Type II alveolar epithelial cells in culture. Type II cells are important in transport/immunological processes across alveolar surfaces.

Example 4

Evaluation of Tissue Function: Vesicle Cycling, and Antigen Uptake and Presentation Primary tissue functionality was tested by checking for vesicle cycling ability and antigen uptake and presentation by the artificial tissue constructs, specifically the Type II epithelial cells. The presence of Type II cells in the epithelium is important for actively bringing antigens across the mucosal barrier. Several techniques were used to identify the cell populations and tissue architecture of the artificial tissue constructs. The presence of Type II epithelial cells is important in a functional alveolar artificial tissue construct, because these cells are primarily responsible for the foreign body response. Both Type I and Type II epithelial cells were identified in the artificial tissue constructs of the present invention. The Type II cells also release surfactant-carrying vesicles. We also demonstrated the immunological function of the type II cells in the bilayer constructs of the present invention.

Figure 2:
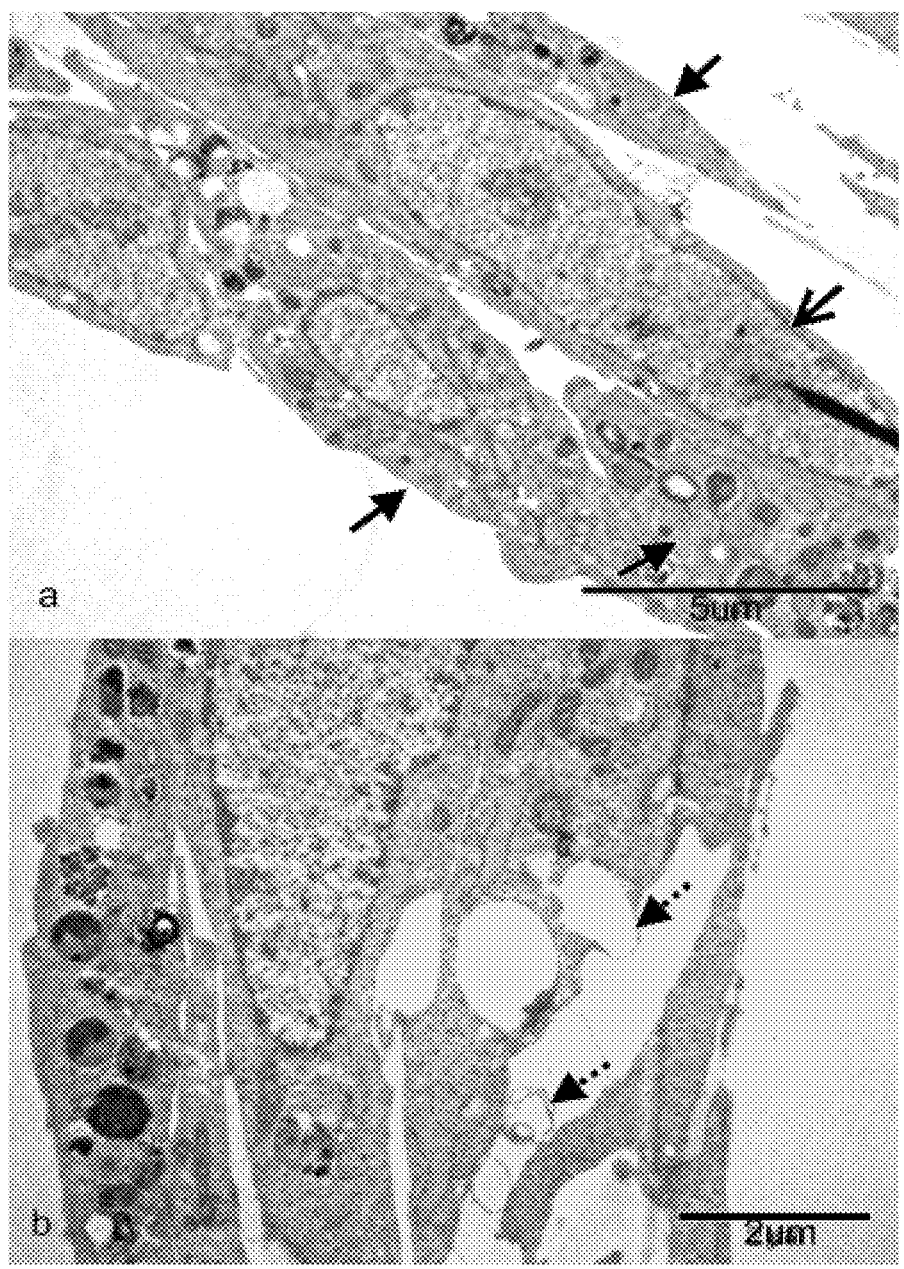
FIG. 2 shows transmission electron microscopy images of epithelial cells. Panel a) shows type II (→) and type I (→) epithelial cells. Panel b) shows type II epithelial cells releasing surfactant carrying vesicles (→).

Transmission electron microscopy (TEM) and immunohistochemical staining of the artificial tissue construct were used to identify Type II cells. Briefly, the cultured epithelial cell cultures were fixed with gluteraldehyde and later exposed to osmium tetroxide. The samples were then embedded in Epon resin, sectioned, and stained with uranyl acetate and lead citrate (FIG. 2). Immunohistochemical staining of the mucosal bilayer was used to identify the epithelium and endothelial monolayers. Epithelial cells in the construct were identified alveolar cell-specific cytokeratin (CK-1, 4, 5, 6, 8, 10, 13, 18, 19) staining. Light microscopy was used to image the cytokeratin-containing epithelial cells mucosal constructs.

The alveolar endothelial cells in the bilayer mucosal construct were identified by Factor VIII staining and light microscopy of the sectioned bilayer tissue. Tissue integrity was visualized by tight junction staining of ZO-1, e-cadherin, and occludins (data not shown).

Example 5

Vesicle Cycling in Epithelial Cells

Confocal microscopy of the constructs was performed at various depths from the surface of the cells (FIG. 2). The total time for vesicle cycling was fixed to ~10 min after the addition of the dye. The results show the presence of an epithelium of approximate 10-µm thickness. No significant level of fluorescence was detected for the endothelium monolayer construct. For the bilayer constructs there is a ~3 µm shift for the epithelium below the endothelium tissue. The ~3-µm shift in vesicle location in the epithelium over endothelium construct can be attributed to the initial cell seeding orientation of the active epithelial cells.

The vesicle cycling activity of Type II cells was visualized with FM143-FX fluorescent dye (FIG. 2). It was shown that the alveolar epithelial cells in the construct were actively forming vesicles around the FM143-FX molecules. However, a need to control the time dependency of this process was identified, as the initial confocal microscopy images showed the presence vesicles over a larger distance.

Example 6

Endpoint Kinetic Analysis of Vesicle Cycling

Figure 3:
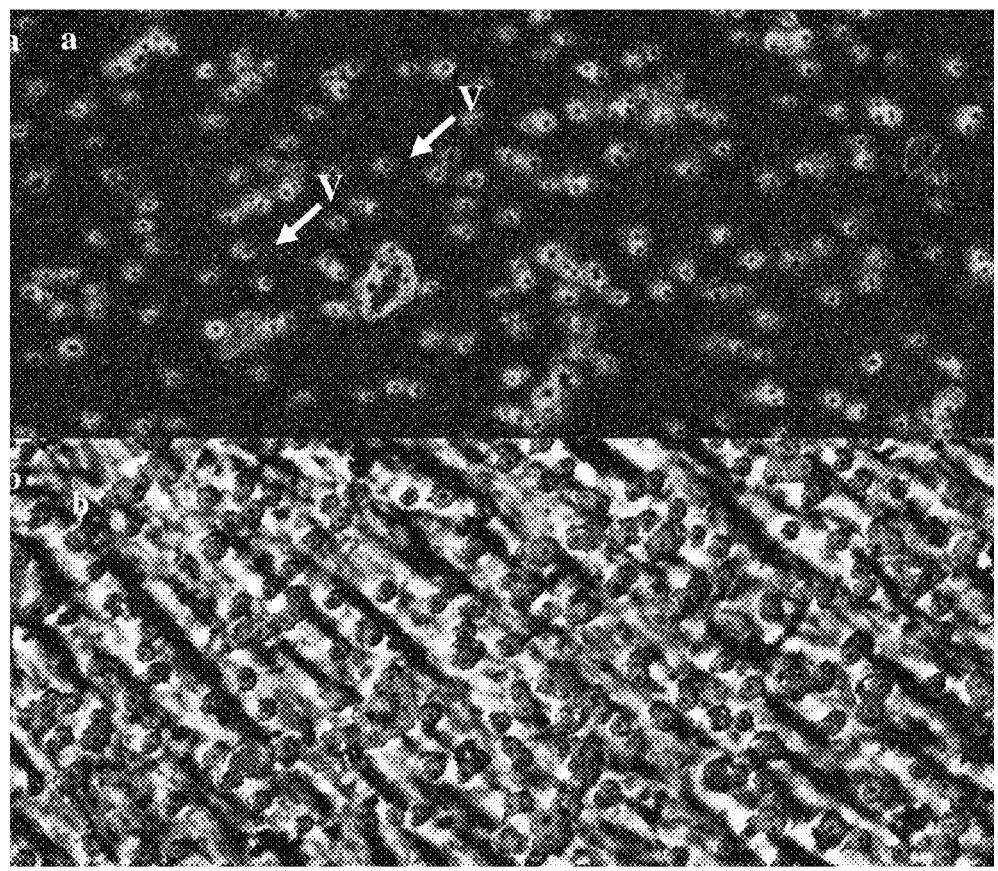
FIG. 3 shows FM-143FX vesicle cycling in a bilayer alveolar mucosal construct. Panel a) is a confocal microscopy image showing fluorescent vesicles (V). Panel b) is a superimposed confocal and light microscopy image showing cells and vesicles.

The endocytotic/exocytotic activity of Type II epithelial cells was visualized with FM-143X. This amphiphilic molecule is non-fluorescent in solution. The alveolar epithelial cells in the construct were indeed actively forming vesicles around the FM-143FX molecules. In this experiment the cells were exposed to FM-143FX for a short time. Confocal microscopy was performed on four different tissue motifs: monolayer epithelium, endothelium and bilayer structures containing epithelium over endothelium, and vice versa. Clear vesicle formation around the fluorescent FM-143FX molecules was visualized in the epithelium over a short time, indicating that the Type II cells in the epithelium were highly active (FIG. 3).

The exact location of the epithelium with respect to the porous plastic support was unclear. In this experiment the cells were exposed to ~5-10 µg/mL of FM-143FX for a fixed period of time (10 min). Confocal microscopy was performed on four different tissue motifs: monolayer epithelium, endothelium and bilayer structures containing epithelium over endothelium and vice versa.

Surfactant vesicles cycling across the mucosal construct were examined. Samples of pure endothelial TE, pure epithelial TE, and combined epithelial/endothelial TE constructs were grown on laminin-coated 24-well collagen Transwell™ cell culture plates. The constructs were stained with FM143-FX to study the activity of the epithelium. Confocal images were recorded at various depths from above and below the surface of the cell layers. Bright fluorescent images were obtained for epithelial and combined epithelial/endothelial constructs, while pure endothelial culture produced negligible fluorescence. The presence of red vacuoles was indicative of active transport of the fluorescent dye by the Type II epithelial cells. This result demonstrated a functional epithelium in the in vitro-cultured constructs.

Example 7

Di-I-Acetylated LDL Endocytosis Method

The di-I-acetylated LDL endocytosis method was used to visualize endothelial cells in the alveolar epithelial and endothelial cell-containing tissue constructs. The presence of red fluorescent dots indicates the location of the fluorescent dye in the endothelial cell layer in the construct. The endothelial cells were cultured on top of the epithelial cells; thus, the dye is not visible in the layer below (the epithelium). Light and fluorescence microscopy superimposed images show the endothelial cell location with respect to the epithelium.

Staining endothelial cells with Di-I-acetylated LDL was performed on non-embedded, non-sectioned epithelial/endothelial constructs. Di-I-acetylated LDL, or 1,1'-dioctadecyl-3,3,3',3'-tetramethyl-indocarbocyanine perchlorate-labeled acetylated low-density lipoprotein enters endothelial cells via receptor-mediated endocytosis and eventually appears in lysosomes. The dye produces intense red fluorescence. 15 µg/mL of DiI acetylated LDL (Invitrogen) was added to two-week-old tissue constructs, containing both epithelial and endothelial cells. Cells were serum-deprived before the addition of DiI acetylated LDL. Samples were incubated for ~3 h at ~37° C. to permit endocytosis of the fluorescent probe. Cells were examined with an Olympus Fluoview FV300™ confocal laser scanning IX-81 biological microscope. The tissue was visualized at various depths to locate the fluorescent DiI acetylated LDL-containing vesicles.

These studies demonstrated the presence of a significant number of Type II epithelial cells in the constructs of the present invention. Staining with amphiphilic fluorescent styryl dye FM143-FX and using depth-stratified confocal imaging confirmed intensive endo- and exocytosis performed by Type II epithelial cells. Staining with anti-pan-cytokeratin (epithelial-specific) and di-I-acetylated-LDL (endothelial-specific) revealed features of epithelial and endothelial components of the combined constructs.

Example 8

Labeled Antigen Uptake by Alveolar Mucosal Cells and HLA-DR Expression

While respiratory mucosal dendritic cells (DCs) serve as primary accessory cells, the resident epithelial cells also function as antigen-presenting cells (APCs) in the upper and lower respiratory mucosa. They also express the MHC class II molecules needed for T cell activation. The large surface area of the respiratory mucosa directly exposes the lung epithelium to airborne antigens.

Figure 4:
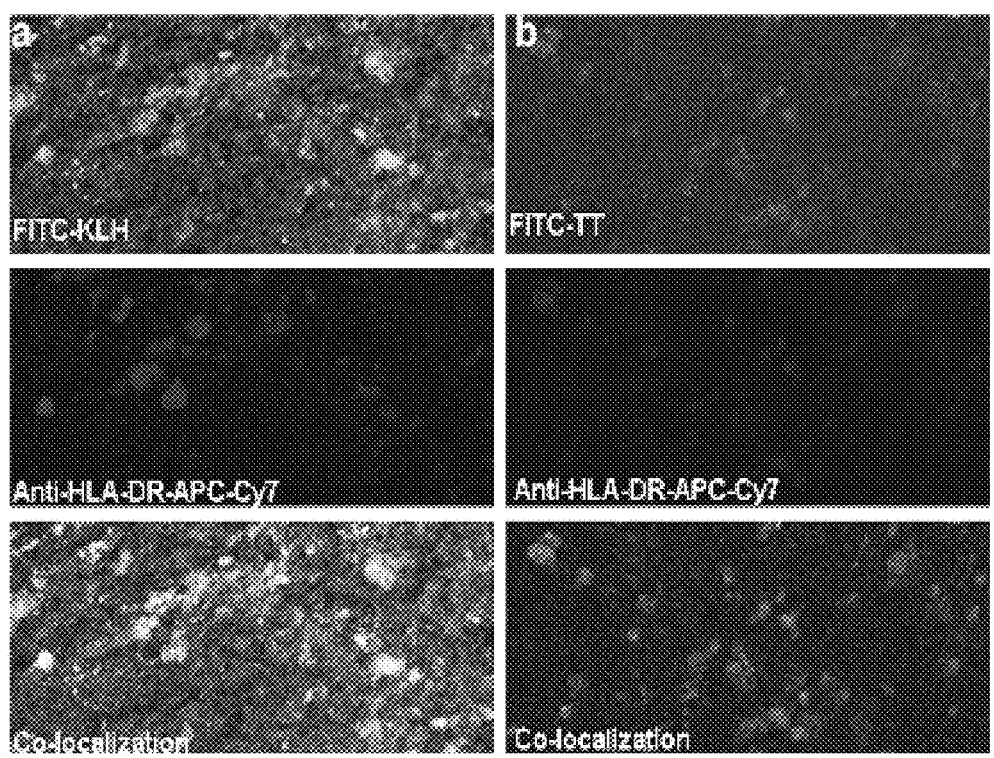
FIG. 4 shows an antigen uptake experiment with lung alveolar mucosal bilayer constructs in the upper row of panels, HLA-DR expression in the middle row of panels, and co-localization of signals in the bottom row. Column a) is KLH. Column b) is TT.

Antigen uptake of fluorescently labeled TT and KLH by the tissue engineered alveolar artificial tissue construct was allowed and later the tissue was stained for HLA-DR to visualize the co-localization of the engulfed antigen and the MHC class II expression by the cells. TT and KLH were labeled with fluorescein isothiocyanate (FITC; 1:5 molar ratio) to create a stable thiourea bond. The labeled product was isolated by membrane filters with appropriate molecular weight cut off. The cells were exposed to the labeled antigen for a period of one hour. The tissue bilayer was then washed with PBS and visualized with confocal microscopy. Anti-HLA-DR-APC-Cy7 was then added to visualize the presence of MHC class II molecules. The tissue was imaged after half an hour after the treatment and subsequent washings (FIG. 4). KLH and TT were successfully labeled and processed by the alveolar artificial tissue constructs where some vesicle-like structures were visualized. It can be seen that most of the HLA-DR signal is localized near the FITC-antigen fluorescence; however there is some low intensity signal by other cells as well. The presence of yellow fluorescence shows co-localization of the captured antigen and HLA-DR expression indicating that the mucosal cells may be useful in presenting antigen to T cells.

Example 9

Effects of Environmental Irritants

Environmental irritants (most often referred to as allergens) are common antigenic compounds that are inhaled, such as molds, ragweed, tree and grass pollens, pet dander, and house dust mites. Grass and house dust mites are the most common environmental irritants, affecting over 22% of the population (Sóti & Endre (2005) Orv Hetil. 146, 833-7).

The effects of, for example, other environmental irritants, such as airborne polycyclic aromatic hydrocarbons, and cigarette smoke-related carcinogens can be examined. Polycyclic hydrocarbons are aromatic organic byproducts of industrial chemical and combustion processes. Respiratory epithelium responds to such compounds by cytochrome P450 enzymatic activity and cytokine production.

The effects of carcinogens, such as 3-methylcholantherene and beta-napthoflavone, and other airborne environmental irritants, such as diesel particles and urban dust, that have been characterized by, for example, NIST (standardized irritants), can be examined using the models of the present invention, as can the effects of cigarette smoke carcinogens, such as nicotine, hydroquinone, and benzopyrene. It has been reported that animals exposed to particulate nicotine exhibit loss of antibody responses to T cell proliferation and an overall immunosuppressive response; data suggests that after binding to nicotine T cells lose their ability to enter cell cycle and proliferate (Sopori et al. (1998) Adv. Exp. Med. Biol. 437, 279-89; Geng et al. (1996) J. Immunol. 156, 2384-9). Hydroquinine and benzopyrene also elicit immunosuppressive responses due to T cell cycle interference (Rodriguez et al. (1999) Immunopharmacol. Immunotoxicol. 21, 379-96; Li et al. (1996) Toxicol. Appl. Pharmacol. 139, 317-23). BioPlex-based assays can be used to monitor cytokine levels in culture media.

Example 10

Effects of Environmental Irritants and Hormones on Constructs

Immunosuppressant effects on the cultured mucosal construct were tested by the addition of, for example, dexamethasone (0.5-0.1 µM) and hydrocortisone (5-10 µM) for 24 h. The effect of, for example, diesel particles (0.01-0.2 mg/mL) and urban dust (0.01-0.2 mg/mL) exposure was also studied in the alveolar tissue. NIST standards Diesel Particulate Matter (SRM 2975), and Urban Dust (SRM 1649a), containing both organic and inorganic components, were used as environmental irritants (FIG. 3). A BioPlex 22-Plex™ cytokine kit (Upstate) was used to quantify the cytokine levels in the collected media.

The cytokine profile of the bilayer construct prepared in a 0.33 cm$^2$ area Transwell™ cell culture device was compared with the alveolar epithelial cells cultured in T-25 flasks. Controls for each experiment with or without the various irritant treatments were also included in the experimental design.

Example 11

Tissue Functionality Evaluation: Cytokine Production

The effects of immunosuppressant hormonal treatment (dexamethasone and hydrocortisone) and exposure to bacterial particles (*E. coli* and *Staphylococcus aureus*) on respiratory cells were examined by quantifying cytokine production by the mucosal tissue. The cellular bilayer was exposed to either high or low levels of hydrocortisone, dexamethasone, or *E. coli* or *S. aureus* particles for 24 h.

Cellular uptake of WST-1 was used to determine the mitochondrial activity of live cells. A spectroscopic reading of the collected/metabolized tetrazolium salt was performed to compare the cellular activity of hormone or bacterial particle treated cells to the non-treated control cells after 24-h treatments. The alveolar artificial tissue construct cells were activated exposure to 3-methylcholanthere while the cells were less activated with the BNF treatments. These results indicated that the bilayer mucosal construct showed similar functionality to primary lung tissue.

Example 12

Bacterial Exposure

The open respiratory system is prone to pathogenic bacterial infections. As examples, *E. coli* (Gram-negative) and *Staphylococcus aureus* (Gram-positive) bacteria can use many substrates as vehicles for growth and transport into the lungs. Both bacteria carry numerous cell surface organelles that help them enter mucosal surfaces, where they cause respiratory illnesses.

The ability of the mucosal constructs to endocytose heat-inactivated, fluorescently labeled bacterial particles was examined. The effects of bacterial treatment on cytokine production by the mucosal models were assessed. Such experiments were conducted with the alveolar artificial tissue construct. Similar experiments can be conducted with a nasopharynx tissue equivalent.

Pro-Inflammatory Cytokine Production after Bacterial Exposure

Figure 5:
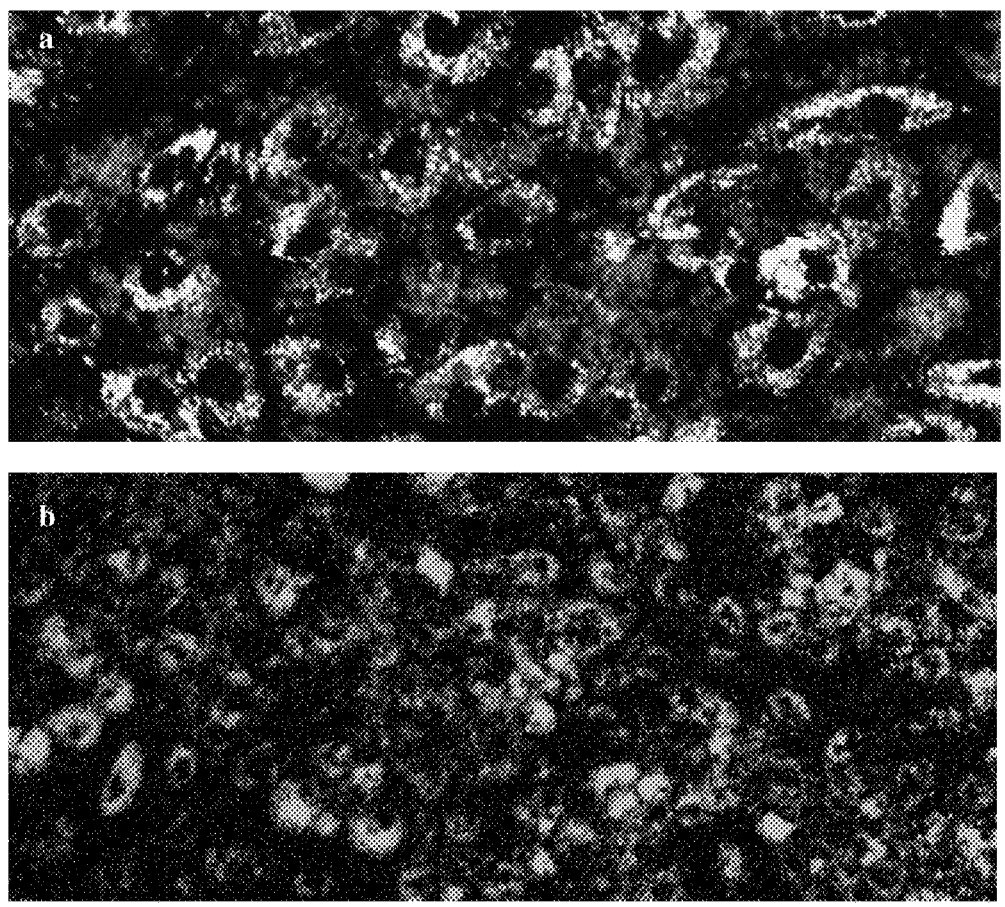
FIG. 5 shows Alexa fluor 488™dye-labeled bacterial transport (24-h exposure) in *E. coli*-treated endothelium and epithelium bilayer (Panel a); 20×) and *S. aureus*-treated endothelium and epithelium bilayer (Panel b); 10×).

For the bacterial particles, fluorescently labeled particles were added to the tissue construct, at control, low, and high levels. Supernatants were collected after a 24-h treatment and fluorescently labeled samples were visualized. Confocal microscopy was performed on heat-inactivated and fluorescently labeled *E. coli* (Alexafluor 488)- and *S. aureus* (Alexafluor 594)-exposed mucosal constructs (FIG. 5).

Figure 6A:
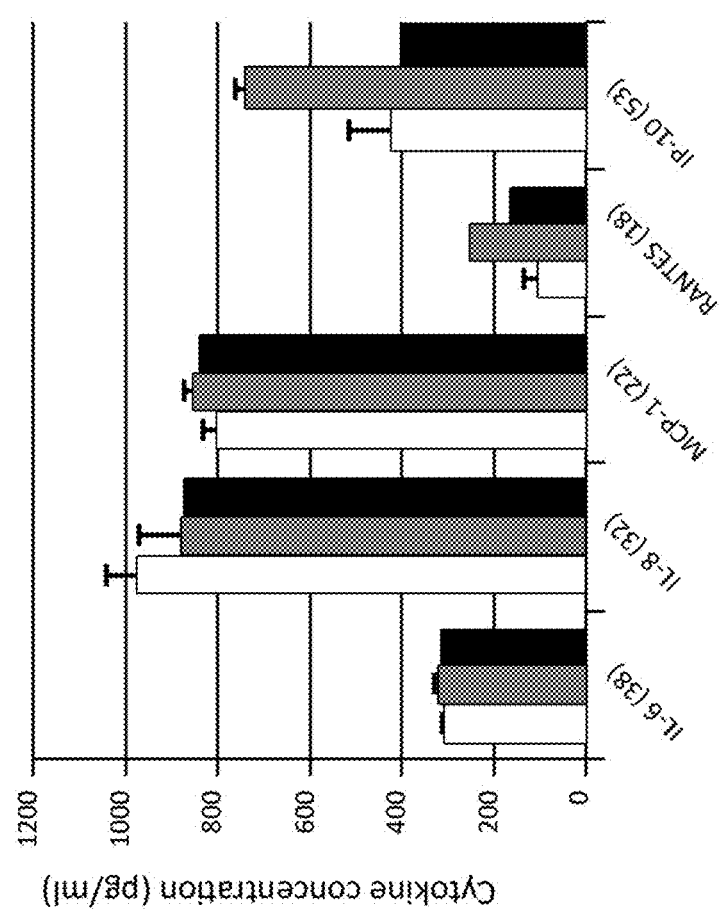
FIGS. 6A-6B are a graphical representation of the effects of bacterial exposure on cytokine production in the bilayer construct. White bars=control; gray bars=*S. aureus*; black bars=*E. coli*.
Figure 6B:
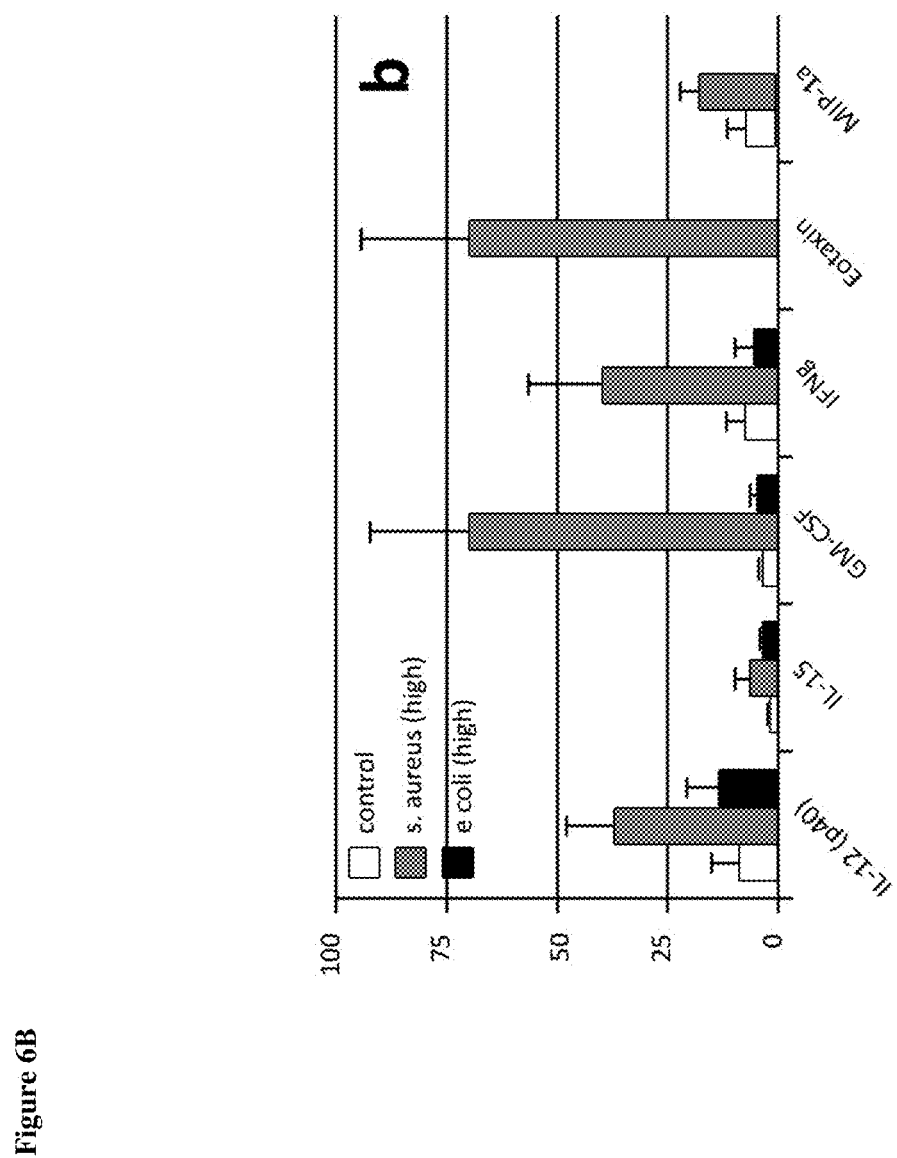

Using Luminex™ immunoassay technology, we simultaneously quantified the 22 cytokine and chemokines in the collected treatment media. This BioPlex kit used is based on ELISA methods with beads coated with 22 antigens. Bacterial treatment significantly increased IL-8 and IL-10, along with IL-1a, IL-12 (p40), GM-CSF and IFN-γ in almost all treatment conditions (FIG. 6).

Example 13

Corticosteroid Treatment

Multiplex analysis of cytokine production along with treatment effects of cellular proliferation were quantified. Surfactant production can be evaluated by, for example, ELISA and immunohistochemical staining methods.

Suppression of Cytokine Production by Corticosteroids

Having established that the constructs of the present invention could be immunostimulated, we next demonstrated that they could be immunosuppressed, by corticosteroids. Corticosteroids are the most widely prescribed drugs for allergic rhinitis and other respiratory diseases that result in a mucosal inflammatory response. Generally, aerosolized local application of these anti-inflammatory medications is non-problematic at levels that do not cause high systemic introduction.

Figure 7A:
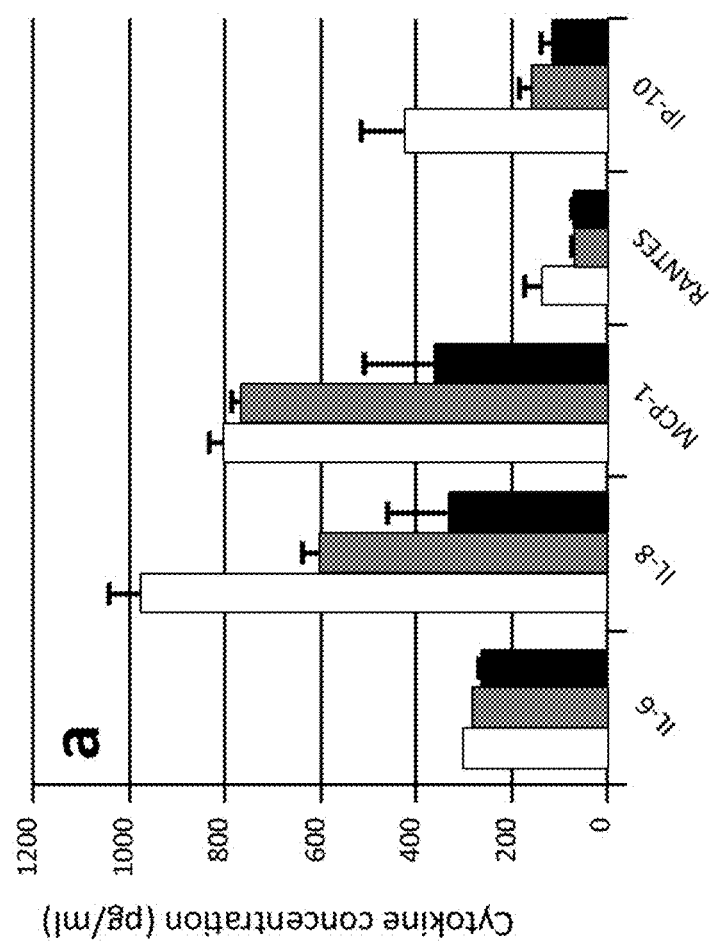
FIGS. 7A-7B are a graphical representation of the effects of hormonal treatment on cytokine production by the bilayer construct. White bars=control; gray bars=hydrocortisone; black bars=dexamethasone.
Figure 7B:
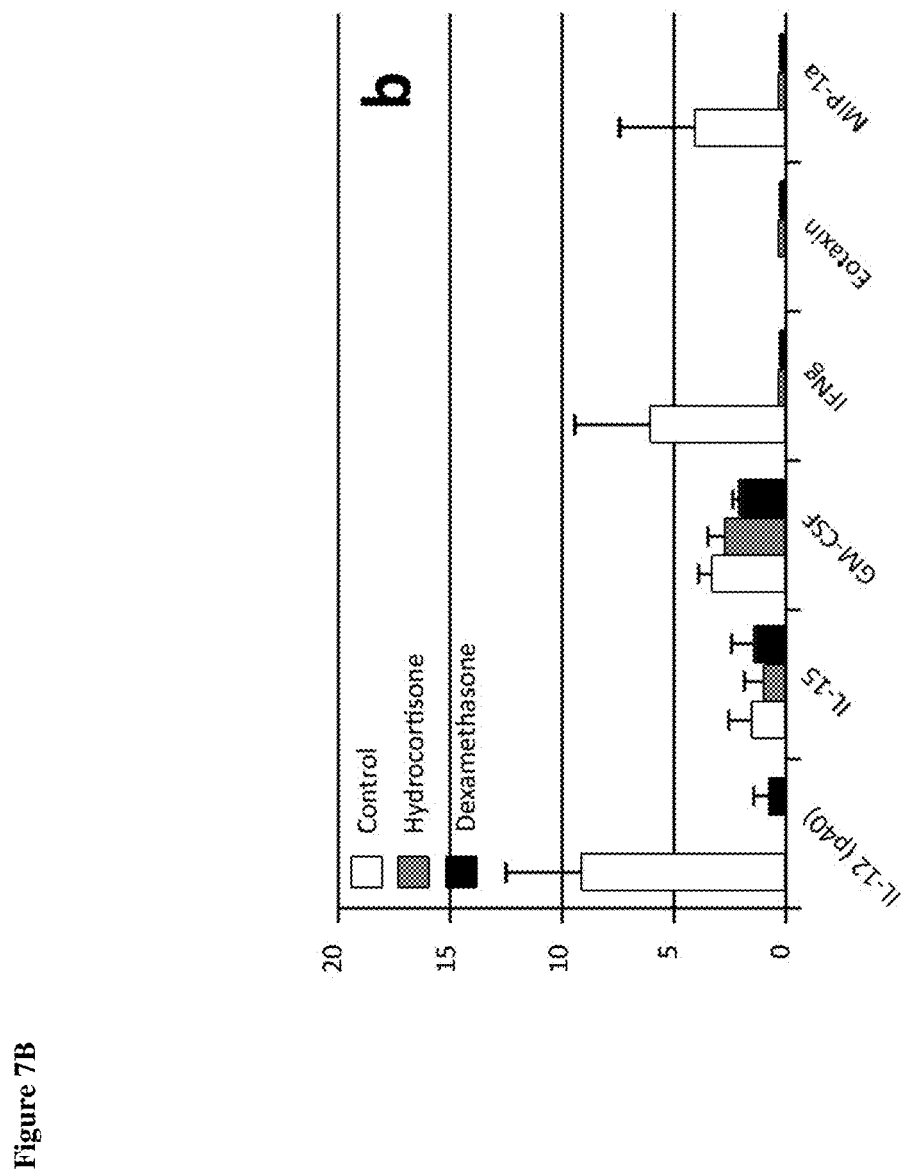

The effects of dexamethasone and hydrocortisone were studied in the in vitro alveolar artificial tissue constructs of the present invention to determine whether the tissue responded to immunosuppressants. The addition of dexamethasone and hydrocortisone to the bilayer mucosal construct resulted in a significant decrease in cytokine production by the native cells (FIG. 7).

The effect of immunosuppressant hormones was clearly observed with GM-CSF, eotaxin, MCP-1, IL-6, IL-8, and IL-12. The epithelial cells cultured in a flask format also showed a decrease in cytokine production compared to the control tissue with the addition of hormones (data not shown here). The particulate treatment of the epithelial cells in flask format induced a reduction in cytokine production. Different irritant concentrations are being considered to relate inflammation to degree of environmental particulate exposure.

Example 14

Tissue Functionality Evaluation: Cytochrome P450 Activity

The effects of polycyclic carcinogens on cytochrome P450 activity in the artificial tissue constructs was also analyzed. Cytochrome P450 proteins are involved in the metabolism of many exogenous and endogenous chemicals, including drugs, steroids, and toxins. Cytochrome P450 induction is indicative of chemical metabolism. Cellular P450 enzyme activity of CYP1A1 & CYP2B1 families was studied. The bilayer constructs were prepared from biopsy samples of three different patients.

The mucosal construct was exposed to either 3-methylcholantherine and β-nitrophenol (FIG. 8) for 24 h, followed by 7-ethoxy resorufin (5-15 µM) or 7-pentoxy resorufin (5-15 µM) addition (for 30 min) to quantify CYP 1A1 and CYP 2B1 activity, respectively. A β-glucuronidase and arylsulfatase enzyme cocktail was then added to the samples and they were incubated for 2 h at 37° C. Fluorometric absorbance was then measured. A standard curve was prepared using resorufin to quantify the P450 activity. 3-Methylcholanthere and β-nitrophenol are known environmental carcinogens found in cigarette smoke and in airborne industrial byproducts.

Figure 8:
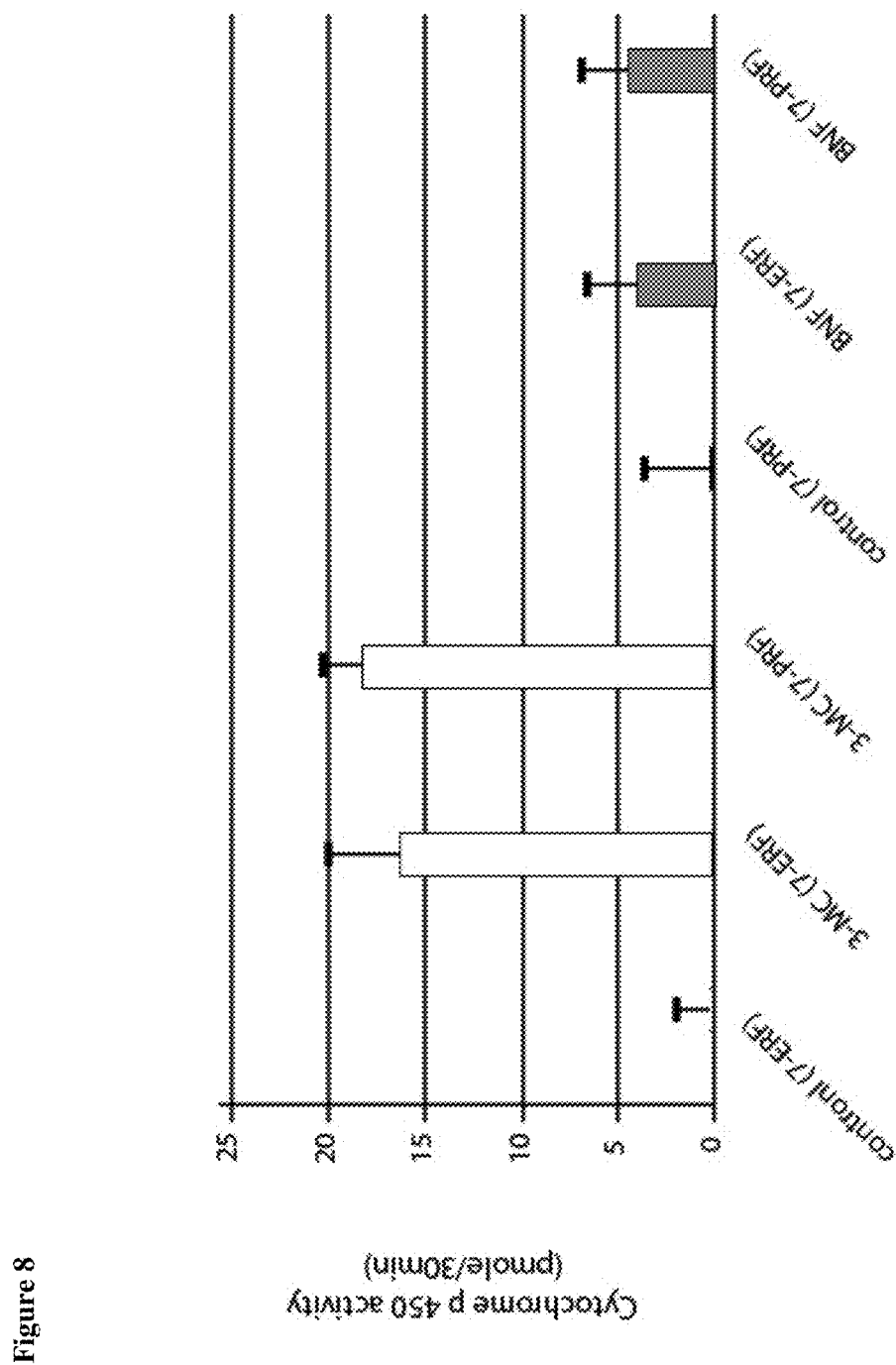
FIG. 8 is a graphical representation of the cytochrome p450 activity of the bilayer mucosal construct. Induction agent: 3-methylcholantherine (3-MC), β-napthophenol (BNF). Detection Assay: 7-ethoxy resorufin (7-ERF), 7-pentoxy resorufin (7-PRF).

Our results showed that the alveolar artificial tissue bilayer construct exhibited p450 (CYP1A1 and CYP2B1) activity when exposed to polycyclic carcinogens. The alveolar artificial tissue construct cells were activated on exposure to 3-methylcholanthere, while the cells were less activated by BNF treatments (FIG. 8). These results show that the bilayer mucosal construct shows similar functionality to primary lung tissues.

Example 15

Surfactant Vesicles Cycling (Qualitative Measurements)

The visualization of surfactant vesicles in the epithelium by transmission electron microscopy, described in example 3, qualitatively shows that the presence and activity of Type II epithelial cells. This was also demonstrated by FM-143FX uptake by the epithelium in the mucosal bilayer construct; shown in example 7.

Example 16

Surfactant Components (Quantitative Measurements)

As examples, release of cytokines and release of lung surfactant by Type II epithelial cells can be assessed, as manifestations of mucosal activity. Cytokines in culture fluids can be measured by multiplex systems. Lung surfactant components can be monitored using commercially available surfactant protein D (SP-D) ELISA kits. More sensitive bead-assisted BioPlex assays can also be used.

Detection of SP-D Using an ELISA Kit

An ELISA kit (AntibodyShop A/S, Denmark) was calibrated according to the manual, using internal standard solutions of SP-D. While the calibration curve remained linear at high concentrations of SP-D, significant drop of registered optical signal at concentrations below ~3-4 ng/mL restricted the practical sensitivity to ~3 ng/mL.

Samples of culture fluid, ~0.5 mL each, were obtained directly from the cultivation wells containing the artificial tissue construct samples, which had been grown for 2 weeks. Samples were serially diluted. The ELISA assay showed that the culture fluids contained less than 1 ng/mL SP-D. A higher sensitivity assay was needed.

We next fabricated SP-D-specific beads for the BioPlex. The bead-assisted SP-D-detection was based on the principal of a sandwich immunosorbent assay, where detection antibodies, coupled with biotin, were attached to a streptavidin-phycoerythrine (SA-PE) fluorescent complex.

A number of polyclonal and monoclonal anti-SP-D antibodies were assessed to assemble the bead-assisted SP-D detection tool. However, most combinations of available antibodies showed no visible detection of the SP-D taken from the standards of the SP-D ELISA kit. Of those tested, only a combination of MAB3132 as a capturing antibody, and detection antibody taken from the SP-D demonstrated measurable sensitivity towards SP-D. The reason for the poor sensitivity to SP-D may have been strong overlapping of the epitopes with the available antibodies.

To demonstrate that the artificial tissue constructs of the present invention possess functional features similar to native mucosa, non-destructive detection of surfactant proteins was conducted. As a test of mucosal functionality, we examined modulation of surfactant release by cytokines and hormones, using non-destructive monitoring. The classic sandwich ELISA was not a useful tool for monitoring surfactant components released by in vitro samples; its sensitivity was insufficient.

Abnova (Taiwan) sells recombinant SP-D fused with a GST tag, and a number of anti-SP-D and anti-GST antibodies. One pair of these antibodies showed sensitivity to SP-D-GST recombinant protein close to 0.02 ng/mL in a sandwich ELISA. The explanation for this impressive sensitivity was apparently the use of a high-affinity anti-GST antibody as the detection antibody. We examined a similar detection system in conditions of direct competition between SP-D-GST and natural SP-D. The presence of the latter in solution should block capturing the fused SP-D-GST, thus eliminating the detection of the GST marker. While more complex and less convenient than a traditional ELISA, such a system can detect low concentrations of surfactant proteins released in the culture fluid.

Other methods for monitoring components of lung surfactant include PCR measurements of mRNA encoding various protein components of the surfactant. This method is destructive, because it requires extraction of RNA from the cells. Immunohistochemical staining of sectioned samples of the constructs can also be used to visualize several components in one run. It is sensitive and informative, but destructive, as it typically requires fixation of the cells. Time-dependent measurements of the fluorescence produced by FM143-FX dye penetrating into lamellar bodies of Type II cells can also be used. The method can be employed semi-non-destructively and is potentially very sensitive.

Example 17

Autologous Blood Compartment

In addition to a bilayer motif of the artificial tissue construct, an autologous blood compartment is added. The model comprises a bilayer tissue engineered structure comprising a polarized epithelium, which serves as a preliminary site of antigen interaction, followed by an endothelial layer, which serves as a barrier between the epithelium and the neutrophil compartment. The in vitro model, the attachment and subsequent migration of peripheral blood leukocytes through the endothelial layer, represents tissue vasculature, followed by transepithelial migration resulting in cellular activation. The contribution of each leukocyte cell population can be dissected to better understand the contributing role of local tissue components.

Peripheral blood mononuclear cells (PBMCs) are isolated from whole blood samples. To minimize red blood cell contamination and remove granulocytes in the limited blood volume, the cell suspension is separated using Histopaque-1077™ mononuclear cell recovery tubes. The Buffy coat interface is collected and repeatedly washed in PBS. The resulting PBMC pellet is disaggregated in cell culture medium containing ~1% serum (~80-95% lymphocytes, ~5-20% monocytes; suspension concentration: ~1×106 white blood cells per mL). Lymphocytes are isolated from the PBMC suspension by plating the white blood cells on TC plates (~1 h, 37° C., ~5% CO2), where monocytes adhere and lymphocytes stay in suspension. Centrifugation of the supernatant (~200 g, ~5 min) yields ~99-100% lymphocyte population. Alternatively, monocytes are isolated from PBMCs using MACS. The isolated PBMCs are incubated with anti-human CD14 antibody-conjugated superparamagnetic microbeads. The labeled suspensions is run through a MACS depletion column (yields ~70-100% monocytes, ~0-30% lymphocyte contamination; ~88-100% purity is acceptable). B and T cells are isolated via negative selection using MACs.

Example 18

Respiratory Syncytial Virus (RSV) and Influenza Infection of Mucosal Models

Respiratory Syncytial Virus (RSV)

The paramyxoviridae family of RNA viruses is characterized by negative-sense single-stranded RNA genomes. Common respiratory human diseases caused by paramyxoviridae viruses include respiratory syncytial virus (RSV), and parainfluenza viruses. The F glycoprotein facilitates fusion with cellular membranes and cell entry. Another relevant cell attachment protein that interacts with sialic acid moieties on the cell surface is "G protein" (Harris & Werling (2003) *Cell Microbiol.* 5, 671-80). Serum titers to RSV are found in the majority of children by the age of two (Glezen et al. (1986) *Am. J. Dis. Child.* 140, 543-6; Chanock & Finberg (1957) *Am. J. Hyg.* 66, 291-300; Chanock et al. (1957) *Am. J. Hyg.* 66, 281-90). Primary RSV infection of the airway epithelium lead to mucus overproduction and an inflammatory response of the tissue and lymphocytes (T cells, B cells, eosinophils, neutrophils) and resultant cytokine, chemokine, and leukotriene production (Becker (2006) *Virus Genes* 33, 235-52; Braciale (2005) *Proc. Am. Thorac. Soc.* 2, 141-6; Garofalo et al. (2001) *J. Infect. Dis.* 184, 393-9; Tripp et al. (2001) *Cell Immunol.* 207, 59-71; Tripp et al. (2000) *Cytokine* 12, 801-7; Tripp et al. (2002) *J. Infect. Dis.* 185, 1388-94; McNamara et al. (2004b) *Lancet* 363, 1031-7; McNamara et al. (2005) *J. Infect. Dis.* 191, 1225-32; McNamara et al. (2004a) *Eur. Respir. J.* 23, 106-12; Falsey (2005) *Exp. Lung Res.* 31 (Suppl 1), 77; Piedimonte et al. (2005) *Pediatr. Pulmonol.* 40, 285-91). Serious sequelae of RSV infection, including bronchiolitis and pneumonia, have been reported in children and the elderly (Collins & Graham (2008) *J. Virol.* 82, 2040-55; Shay et al. (1999) *JAMA* 282, 1440-6; Falsey (2005) *Exp. Lung Res.* 31 (Suppl 1), 77; Ottolini & Hemming (1997) *Drugs* 54, 867-84; Wyde (1998) *Antiviral Res.* 39, 63-79). Reliable animal models of RSV infection and pathology remain elusive (Byrd & Prince (1997) *Clin. Infect. Dis.* 25, 1363-8).

Various therapeutic approaches have been explored for RSV infection. An initial vaccine effort entailed the use of formalin-inactivated virus, which actually exacerbated disease in a number of recipients (Hall (1994) *Science* 265, 1393-4; Dudas & Karron (1998) *Clin. Microbiol. Rev.* 11, 430-9). Subunit RSV vaccines with modified G and F glycoproteins have shown limited efficacy in children under the age of 12 and in patients with chronic lung disease (Dudas & Karron (1998) *Clin. Microbiol. Rev.* 11, 430-9; Venkatesh & Weisman (2006) *Expert Rev. Vaccines* 5, 261-8). A live attenuated virus vaccine approach, employing reverse genetics, has shown some success after initial failures with attenuation and lack of temperature sensitivity (Collins & Murphy (2005) *Proc. Am. Thorac. Soc.* 2, 166-73). Protein-modified viral vaccines exhibit stable phenotype but lacked attenuation; there was some improvement with genetically engineered cpts/404/1030 (Dudas & Karron (1998) *Clin. Microbiol. Rev.* 11, 430-9; Whitehead et al. (1999a) *J. Virol.* 73, 871-7; Whitehead et al. (1999b) *J. Virol.* 73, 9773-80). Enhanced efficacy has been shown in passive immunization approaches with monoclonal antibodies, such as Synagis (palivizumab) and its improved derivative, motavizumab; however, little is known about these monoclonal antibodies that interact with F and G proteins and the pathways leading to the induction of immunity (Weltzin (1998) *Expert Opin. Investig. Drugs* 7, 1271-83; Johnson et al. (1999) *J. Infect. Dis.* 180, 35-40; Johnson et al. (1997) *J. Infect. Dis.* 176, 1215-24).

Example 19

Palvizumab Evaluation

The artificial tissue constructs of the present invention can be used to evaluate, for example, palvizumab. Neutralizing IgGs are believed to play a role in abrogating the transit of upper tract RSV infection to the lower respiratory tract. These antibodies are directed towards the F and G surface proteins. To study the efficacy of the anti-F protein mAb palvizumab in our alveolar artificial tissue constructs, the mucosal tissue can be infected with the Long strain of RSV and then treated with palvizumab, a commercially available monoclonal anti-RSV antibody.

The artificial tissue constructs can be infected with serial of dilutions of the Long strain RSV for a minimum of ~2 h at ~37° C., using for example, up to a thousand-fold $TCID_{50}$ dilution of the virus. After removal of excess virus, the artificial tissue construct can be cultured from ~2 h up to ~5 days. The replication of RSV can be determined by F protein expression, using, for example, ELISA-based methods. The tissue construct is then fixed and incubated with biotin-conjugated anti-F protein monoclonal antibody, and labeled with a secondary antibody, followed by a spectrophotometric read-out. The neutralizing titer is defined as the antibody concentration that results in 50% or more reduction in the spectrophotometric read-out. RSV-infected cells will be compared against non-treated controls. The effects of RSV infection of cellular viability can also be evaluated as this may affect the monoclonal antibody interaction. The cytokine profile of the infected and non-infected cells before and after palvizumab treatment can also be quantified by, for example, multiplex analysis of the culture supernatants. T cell functionality and proliferation can also be evaluated.

Example 20

Influenza

Despite considerable research efforts over recent decades, influenza virus continues to have a significant impact on the human population, worldwide (Kitler et al. (2002) *Vaccine* 20 (Suppl 2) S5-14; Monto (2000) *Am. J. Manag. Care* 6 (5

Suppl) 5255-64). Common flu or influenza belongs to the Orthomyxoviridae family of enveloped, negative-sense segmented RNA viruses, and influenza A, influenza B, and influenza C are the common strains. Although types A and B are responsible for most human infections, type A strains are considered more virulent and have been the primary focus of numerous therapeutic approaches for understanding and treating the disease. Type A influenza is defined by its two important surface antigenic proteins; hemagglutinin, HA (16 subtypes) and neuraminidase, NA (9 subtypes). The virus uses HA and NA for attachment and movement through the respiratory mucosal membrane. Hemagglutinin binds to sialic acid, resulting in viral attachment and fusion. Neuraminidase is involved in removal of sialic acid moieties that allows the virus to move though the mucosal surfaces after pinching off from the cellular membranes. HA and NA are also the antigenic sites of interaction with neutralizing antibodies that prevent viral infection and replication. Due to its relatively high degree of mutability, the influenza viruses continue to undergo antigenic drift (e.g., mutation of HA, NA surface proteins) and shift (due to its segmented RNA genome allowing re-assortment of two viral genomes in the same host). These alterations in viral phenotype can result in the virus evading the host immune system and serving as the impetus for the annual reformulation of the trivalent influenza vaccine (Zambon (1999) *J. Antimicrob. Chemother.* 44 (Suppl B), 3-9).

MedImmune's cold-adapted live-attenuated influenza vaccine FluMist® has been shown to offer protective immunity against mis-matched vaccine strains, suggesting a broader palette of immune response to this 'live' vaccine. The efficacy of the vaccine has been suggested to be the result of multiple attenuating effects on several genes (Jin et al. (2003) *Virology* 306, 18-24). This vaccine has been shown to be as effective as the inactivated viral vaccine in healthy people (5 to 49 years of age). However, the mechanism(s) by which it induces protective mucosal immunity remain(s) unclear.

Immunological Characterization with FluMist® Vaccine

The in vitro respiratory mucosal models of the present invention can be used to evaluate, for example, FluMist® vaccine. The in vitro mucosal immunological model of the present invention can be used to assess viral transport processes as they relate to the efficacy of immune response induction. The mucosal tissue equivalent can be infected with the cold-adapted, temperature-sensitive live attenuated influenza trivalent FluMist® vaccine. To examine the immunological properties of the construct, the H1N1 strain in the FluMist® vaccine can be evaluated. The replication efficiency and delivery at the nasal passage temperature (~25-28° C.), nasopharynx temperature (~34° C.), and lung temperature (~37° C.) can be studied to further evaluate the constructs. Results obtained can be compared with published clinical reviews on the efficacy of the vaccine in the clinical setting (Wiselka (1998) Vaccine Safety, Textbook of Influenza. Blackwell Sciences; Keitel et al. (2001) *J. Infect. Dis.* 183, 329-332).

The mucosal construct is infected with the H1N1 strain in FluMist® vaccine at the median tissue culture infectious dose ($TCID_{50}$) administered to patients. The construct is placed in an incubator at 34° C. The corresponding control is placed at 37° C. FITC-labeled H1N1 viral antibodies (Chemicon Inc, Argene, Inc) are used to detect the presence and location of the virus. For example, the degree of infection can be quantified by labeling the remaining viral particles in the inocula. Fusion events can be imaged by confocal microscopy. The intensity of the fluorescent signal is expected to increase once a fusion event and acidification occurs. The labeled antibody is introduced to the virally infected construct after a period of time. Alternatively, the fluorescent antibody is attached to the virus before exposure to the cells. Anti-MDV antibodies (Biodesign Inc.) can be used to detect the degree of infection in a defined construct surface area. The infected constructs can be fixed with a gluteraldehyde-based fixative and embedded in an EPON-like polymer for high-resolution transmission electron microscopy imaging. Inflammation in the infected tissue can be quantified using, for example, ELISA-based methods. The multiplex bead array Technique™ (BioPlex) can also be used to monitor cytokine levels in small volume samples of culture fluids and donor sera. Culture media from infected constructs can be used to quantify the cytokine response. The influenza virus can be inactivated with, for example, β-propiolactone (BPL) or similar chemicals to prepare the samples for metabolic testing.

A combination of functional assays can be used to determine the degree of viral infection, neutralization and effective dose needed at various temperatures. For each donor, humoral immune responses to FluMist® vaccine in the mucosal construct can be evaluated with, for example, ELISA- and BioPlex-based methods. Media collected at days 1, 4, 7, and 11 can be serially diluted and added to hemagglutinin-coated plates, followed by conjugation with a secondary antibody directed against the immunoglobulin. Additionally, the Bioplex system, using beads coated with the specific hemagglutinin molecules in the FluMist® vaccine, can delineate the contribution of each vaccine component to the overall antibody response. Total IgA, IgG, and IgM can be quantified by, for example, a sandwich ELISA technique using standard human serum for the standard curve. Viral neutralization assays using collected media can be performed by reintroduction to respiratory mucosal bilayer construct followed by, for example, FITC or another fluorescently labeled anti-influenza A monoclonal antibody. After treatment, the absence of a fluorescent signal is indicative of viral neutralization and fluorescent cells indicate viral infection. Hemagglutination inhibition antibody titers can be tested in the collected media by standard microtiter methods.

Primary epithelial and endothelial cells from various donors can be tested to check the degree of infection with each of the FluMist® vaccine strains. A wider range of temperature, viral concentration and donor age may be examined in the mucosal construct.

All documents, publication, manuals, article, patents, summaries, references and other materials cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. An artificial tissue construct comprising:

(a) a first confluent cellular layer comprising alveolar primary epithelial cells, and (b) a second confluent cellular layer comprising alveolar primary endothelial cells, wherein the first layer is stacked on top of and in direct contact with the second layer, or wherein the second layer is stacked on top of and in direct contact with the first layer.

2. The artificial tissue construct of claim 1, wherein the alveolar primary epithelial cells are human cells.

3. The artificial tissue construct of claim 1, wherein the alveolar primary endothelial cells are human cells.

4. The artificial tissue construct of claim 1, wherein the alveolar primary epithelial cells and the alveolar primary endothelial cells are human cells.

5. The artificial tissue construct of claim 4, wherein the human alveolar primary endothelial cells and the human alveolar primary epithelial cells are from the same human.

6. An in vitro cell culture comprising an artificial tissue construct of claim 4 and culture media comprising red blood cells or white blood cells.

7. An in vitro cell culture comprising an artificial tissue construct of claim 4 and culture media comprising one or more of monocytes, CD4+ T lymphocytes, CD8+ T lymphocytes, B lymphocytes, and natural killer cells.

8. The artificial tissue construct of claim 1, further comprising primary alveolar macrophages.

9. The artificial tissue construct of claim 8, wherein the primary alveolar macrophages are interspersed among the alveolar primary epithelial cells and the alveolar primary endothelial cells.

10. The artificial tissue construct of claim 8, wherein the primary alveolar macrophages are interspersed among the alveolar primary epithelial cells and the alveolar primary endothelial cells, and positioned between the first cellular layer and the second cellular layer.

11. An in vitro cell culture comprising an artificial tissue construct of claim 8 and culture media comprising red blood cells or white blood cells.

12. An in vitro cell culture comprising an artificial tissue construct of claim 8 and culture media comprising one or more of monocytes, CD4+ T lymphocytes, CD8+ T lymphocytes, B lymphocytes, and natural killer cells.

13. The artificial tissue construct of claim 1, wherein the first layer is stacked on top of and in direct contact with the second layer, and wherein the second layer is position on a biocompatible membrane.

14. The artificial tissue construct of claim 13, wherein the biocompatible membrane is selected from the group consisting of basement membrane, extracellular matrix, collagen, laminin, proteoglycan, vitronectin, fibronectin, poly-D-lysine and polysaccharide.

15. The artificial tissue construct of claim 13, wherein the biocompatible membrane is an extracellular matrix comprising laminin and collagen.

16. An in vitro cell culture comprising an artificial tissue construct of claim 13 and culture media comprising red blood cells or white blood cells.

17. An in vitro cell culture comprising an artificial tissue construct of claim 13 and culture media comprising one or more of monocytes, CD4+ T lymphocytes, CD8+ T lymphocytes, B lymphocytes, and natural killer cells.

18. An in vitro cell culture comprising an artificial tissue construct of claim 1 and culture media comprising red blood cells or white blood cells.

19. An in vitro cell culture comprising an artificial tissue construct of claim 1 and culture media comprising one or more of monocytes, CD4+ T lymphocytes, CD8+ T lymphocytes, B lymphocytes, and natural killer cells.

20. The artificial tissue construct of claim 19, wherein the culture media comprises a population of B lymphocytes, or a population of B lymphocytes and T lymphocytes.

* * * * *